US 11,857,623 B2

(12) United States Patent
Sabban

(10) Patent No.: US 11,857,623 B2
(45) Date of Patent: Jan. 2, 2024

(54) PAN-ANTIALLERGY VACCINE

(71) Applicant: King Abdulaziz University, Jeddah (SA)

(72) Inventor: Sari Sabban, Jeddah (SA)

(73) Assignee: King Abdulaziz University, Jeddah (SA)

( * ) Notice: Subject to any disclaimer, the term of this patent is extended or adjusted under 35 U.S.C. 154(b) by 479 days.

(21) Appl. No.: 16/988,076

(22) Filed: Aug. 7, 2020

(65) Prior Publication Data

US 2022/0040296 A1  Feb. 10, 2022

(51) Int. Cl.
*A61K 39/395* (2006.01)
*A61K 39/00* (2006.01)

(52) U.S. Cl.
CPC ...... *A61K 39/395* (2013.01); *A61K 2039/544* (2013.01); *A61K 2039/555* (2013.01)

(58) Field of Classification Search
None
See application file for complete search history.

(56) References Cited

U.S. PATENT DOCUMENTS

| | | | |
|---|---|---|---|
| 6,887,472 B2 * | 5/2005 | Morsey | A61P 27/14 |
| | | | 424/134.1 |
| 8,865,179 B2 | 10/2014 | Chen | |
| 9,187,553 B2 * | 11/2015 | Chen | A61K 39/0008 |
| 9,688,978 B2 | 6/2017 | Buechler et al. | |

OTHER PUBLICATIONS

Azoitei et al. "Computation-guided backbone grafting of a discontinuous motif onto a protein scaffold." Science (New York, N.Y.) vol. 334,6054 (2011): 373-6. doi:10.1126/science.1209368 (Year: 2011).*
Stryer, Biochemistry 4th, WH Freeman, New York. 1995 (Year: 1995).*
Sabban, Sari S. "Computationally grafting an IgE epitope onto a scaffold: Implications for a pan anti-allergy vaccine design." Computational and structural biotechnology journal vol. 19 4738-4750. Aug. 14, 2021, doi:10.1016/j.csbj.2021.08.012 (Year: 2021).*
Structural Genomics Consortium., Architecture et Fonction des Macromolécules Biologiques., Berkeley Structural Genomics Center. et al. Protein production and purification. Nat Methods 5, 135-146 (2008). (Year: 2008).*
Baltabekova, et al. ; Presentation of Receptor-Contacting Loop of Human IgE on the HBCAG Particles ; CBU International Conference on Innovation, Technology Transfer and Education ; Mar. 25-27, 2015 ; 8 Pages.
Chen ; Broadly neutralizing(BN) pan-IgE supersite vaccine for allergic asthma ; IgE Therapeutics, Inc. ; Oct. 22, 2019 ; Abstract Only ; 3 Pages.
Chen, et al. ; Protection of IgE-medicated allergic sensitization by active immunization with IgE loops constrained in GFP protein scaffold ; Journal of Immunological Methods, vol. 333, Issues 1-2 ; pp. 10-23 ; Apr. 2008 ; Abstract Only ; 2 Pages.

* cited by examiner

*Primary Examiner* — Michael Szperka
*Assistant Examiner* — Lia E Taylor
(74) *Attorney, Agent, or Firm* — Oblon, McClelland, Maier & Neustadt, L.L.P.

(57) ABSTRACT

The invention is directed to a protein construct comprising a scaffold protein into which an IgE epitope containing motif is inserted or substituted. The protein construct may be used as an antigen, immunogen or vaccine to induce immune responses against IgE in a vaccinated subject thereby reducing the severity of allergic phenomena associated with IgE. The invention is also directed to a method for designing such a protein construct and expressing it using recombinant DNA methods.

14 Claims, 17 Drawing Sheets

Specification includes a Sequence Listing.

Design # 1

Lowest simulated structure: 0.519 Å

GVHVPFTVTHPHLPRALSSHLQFNKDQEILFEQLAKKVMRVLKEQLGID
EEEARRAKQVSFIVYFKDGSSTKIDGSSDEHEENKINAAEIKKIEVKVD

Design # 2

Lowest simulated
structure: 0.543 Å

GVQVPFTVTHPHLPRALSSHLTFNKDQEILYEELAKKVMRVLEEQLGIT
EEEARRAKQVKFVVYFKDGSSTEIDGSSDEHEENKINAAEIKKIEVKVD

Design # 3

Lowest simulated structure: 0.413 Å

GVQVPYTVTHPHLPRALSSHLTFNKDQEILYEQLAKKVMKVAEEKLGI
TEEEARRAKQFKFVVYFKDGSSTEIDGKSDEHEENKINAAEIKKIEVKID

Design # 4

Lowest simulated structure: 0.701 Å

GVTVPYTVTHPHLPRALSSHLTFNKDQEILYEQLAKKVMKVLEKQLGIS
EEEARRAKQVKFVVYFKDGSSTEIDGSSDEHEENKINAAEIKKIEVKVD

Design # 5

Lowest simulated structure: 0.712 Å

GVTVPFTVTHPHLPRALKSELTFKKDQEILFEHLAAEVKRVLEEKQGIT
EEEAKRAKQVKFVVYFKDGSSKEIDGSSSEHEQRKINAAEIKKIEVKID

Design # 6

Lowest simulated structure: 0.581 Å

GTKVPYEVTHPHLPRALHSHLEFEKDKEILFEHLAKKVKEVLKKERGIS
EEEARRAKQVKFVVYFKDGSSQEIDGSSDESKDNKINAAEIKKISVNVD

Design # 7

Lowest simulated structure: 0.479 Å

GTHVPFTVTHPHLPRALSDHLEYEKDKRVLLEEIAKKVKEVLKKKRGI
SEEEARRAKQVSFIIFFKDGSSKKVDGSSDESKRDEVDAAKIKKIEINVD

Design # 8

Lowest simulated structure: 0.556 Å

GTRVPFKVTHPHLPRALESELEFEKDKEILFEELAKKVKEMAKKQRGIS
EEEARRAKQFKFIVYFKDGSSQEIDGKSDESEDNKINAAEIKKIEVHVD

Design # 9

Lowest simulated structure: 0.827 Å

GTTVPFTVTHPHLPRALSSELEFEKDKEILFEELLKKVKEMLKKQRGI
SEEEARRAKQVKFIVYFKDGSSQEIDGSSDEHKENKINAAEIKKIEVHVD

Design # 10

Lowest simulated structure: 0.574 Å

GTTVPFHVTHPHLPRALQSELEFEKDKEILLEHLAKKVKEVLKKQRGISE
EEAKRAKQVKFVVYFKDGSSKEVDGSSEESEDDKINAAEIKKISVNVD

SEQUENCE LISTING

```
<160> NUMBER OF SEQ ID NOS: 25

<210> SEQ ID NO 1
<211> LENGTH: 327
<212> TYPE: PRT
<213> ORGANISM: Homo sapiens
<220> FEATURE:
<221> NAME/KEY: MISC_FEATURE
<222> LOCATION: (1)..(327)
<223> OTHER INFORMATION: Chain B, IG EPSILON CHAIN C REGION PDB: 2Y7Q_B

<400> SEQUENCE: 1

Asp Ile Val Ala Ser Arg Asp Phe Thr Pro Pro Thr Val Lys Ile Leu
1               5                   10                  15

Gln Ser Ser Cys Asp Gly Gly Gly His Phe Pro Pro Thr Ile Gln Leu
            20                  25                  30

Leu Cys Leu Val Ser Gly Tyr Thr Pro Gly Thr Ile Gln Ile Thr Trp
        35                  40                  45

Leu Glu Asp Gly Gln Val Met Asp Val Asp Leu Ser Thr Ala Ser Thr
    50                  55                  60

Thr Gln Glu Gly Glu Leu Ala Ser Thr Gln Ser Glu Leu Thr Leu Ser
65                  70                  75                  80
```

```
Gln Lys His Trp Leu Ser Asp Arg Thr Tyr Thr Cys Gln Val Thr Tyr
                85                  90                  95

Gln Gly His Thr Phe Glu Asp Ser Thr Lys Lys Cys Ala Asp Ser Asn
            100                 105                 110

Pro Arg Gly Val Ser Ala Tyr Leu Ser Arg Pro Ser Pro Phe Asp Leu
        115                 120                 125

Phe Ile Arg Lys Ser Pro Thr Ile Thr Cys Leu Val Val Asp Leu Ala
    130                 135                 140

Pro Ser Lys Gly Thr Val Gln Leu Thr Trp Ser Arg Ala Ser Gly Lys
145                 150                 155                 160

Pro Val Asn His Ser Thr Arg Lys Glu Glu Lys Gln Arg Asn Gly Thr
                165                 170                 175

Leu Thr Val Thr Ser Thr Leu Pro Val Gly Thr Arg Asp Trp Ile Glu
            180                 185                 190

Gly Glu Thr Tyr Gln Cys Arg Val Thr His Pro His Leu Pro Arg Ala
        195                 200                 205

Leu Met Arg Ser Thr Thr Lys Thr Ser Gly Pro Arg Ala Ala Pro Glu
    210                 215                 220

Val Tyr Ala Phe Ala Thr Pro Glu Trp Pro Gly Ser Arg Asp Lys Arg
225                 230                 235                 240

Thr Leu Ala Cys Leu Ile Gln Asn Phe Met Pro Glu Asp Ile Ser Val
                245                 250                 255

Gln Trp Leu His Asn Glu Val Gln Leu Pro Asp Ala Arg His Ser Thr
            260                 265                 270

Thr Gln Pro Arg Lys Thr Lys Gly Ser Gly Phe Phe Val Phe Ser Arg
        275                 280                 285

Leu Glu Val Thr Arg Ala Glu Trp Glu Gln Lys Asp Glu Phe Ile Cys
    290                 295                 300

Arg Ala Val His Glu Ala Ala Ser Pro Ser Gln Thr Val Gln Arg Ala
305                 310                 315                 320

Val Ser Val Asn Pro Gly Lys
                325

<210> SEQ ID NO 2
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: An FG motif
<220> FEATURE:
<221> NAME/KEY: MISC_FEATURE
<222> LOCATION: (1)..(10)
<223> OTHER INFORMATION: Residues 420-429 of SEQ ID NO: 1

<400> SEQUENCE: 2

Val Thr His Pro His Leu Pro Arg Ala Leu
1               5                   10

<210> SEQ ID NO 3
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: Receptor binding site ("R") which comprises
      residues 331-338 of 2Y7Q chain B.

<400> SEQUENCE: 3
```

```
<210> SEQ ID NO 4
<211> LENGTH: 188
<212> TYPE: PRT
<213> ORGANISM: Homo sapiens
<220> FEATURE:
<221> NAME/KEY: MISC_FEATURE
<222> LOCATION: (1)..(188)
<223> OTHER INFORMATION: IgE receptor, 2Y7Q chain A

<400> SEQUENCE: 4

Glu Thr Gly Val Pro Gln Lys Pro Lys Val Ser Leu Asn Pro Pro Trp
1               5                   10                  15

Asn Arg Ile Phe Lys Gly Glu Asn Val Thr Leu Thr Cys Asn Gly Asn
            20                  25                  30

Asn Phe Phe Glu Val Ser Ser Thr Lys Trp Phe His Asn Gly Ser Leu
        35                  40                  45

Ser Glu Glu Thr Asn Ser Ser Leu Asn Ile Val Asn Ala Lys Phe Glu
    50                  55                  60

Asp Ser Gly Glu Tyr Lys Cys Gln His Gln Gln Val Ala Glu Ser Glu
65                  70                  75                  80

Pro Val Tyr Leu Glu Val Phe Ser Asp Trp Leu Leu Leu Gln Ala Ser
                85                  90                  95

Ala Glu Val Val Met Glu Gly Gln Pro Leu Phe Leu Arg Cys His Gly
            100                 105                 110

Trp Arg Asn Trp Asp Val Tyr Lys Val Ile Tyr Tyr Lys Asp Gly Glu
        115                 120                 125

Ala Leu Lys Tyr Trp Tyr Glu Asn His Ala Ile Ser Ile Thr Asn Ala
    130                 135                 140

Ala Ala Glu Asp Ser Gly Thr Tyr Tyr Cys Thr Gly Lys Val Trp Gln
145                 150                 155                 160

Leu Asp Tyr Glu Ser Glu Pro Leu Asn Ile Thr Val Ile Lys Ala Pro
                165                 170                 175

Arg Glu Lys Gly Thr Lys His His His His His His
            180                 185

<210> SEQ ID NO 5
<211> LENGTH: 98
<212> TYPE: PRT
<213> ORGANISM: Staphylococcus aureus
<220> FEATURE:
<221> NAME/KEY: MISC_FEATURE
<222> LOCATION: (1)..(98)
<223> OTHER INFORMATION: Chain A, Crystal Structures Of Eap Domains From
      Staphylococcus Aureus Reveal An Unexpected Homology To Bacterial
      Superantigens

<400> SEQUENCE: 5

Gly Ser Thr Val Pro Tyr Thr Ile Thr Val Asn Gly Ser Gln Asn
1               5                   10                  15

Ile Leu Ser Asn Leu Thr Phe Asn Lys Asn Gln Asn Ile Ser Tyr Lys
            20                  25                  30

Asp Leu Glu Gly Lys Val Lys Ser Val Leu Glu Ser Asn Arg Gly Ile
        35                  40                  45

Thr Asp Val Asp Leu Arg Leu Ser Lys Gln Ala Lys Tyr Thr Val Asn
    50                  55                  60

Phe Lys Asn Gly Thr Lys Lys Val Ile Asp Leu Lys Ser Gly Ile Tyr
```

65                  70                  75                  80

Thr Ala Asn Leu Ile Asn Ser Ser Asp Ile Lys Ser Ile Asn Ile Asn
                85                  90                  95

Ile Asp

<210> SEQ ID NO 6
<211> LENGTH: 10
<212> TYPE: PRT
<213> ORGANISM: Staphylococcus aureus
<220> FEATURE:
<221> NAME/KEY: MISC_FEATURE
<222> LOCATION: (1)..(10)
<223> OTHER INFORMATION: Positions 164-173 of the A chain of the 1YN3
      protein

<400> SEQUENCE: 6

Ile Thr Val Asn Gly Thr Ser Gln Asn Ile
1               5                   10

<210> SEQ ID NO 7
<211> LENGTH: 98
<212> TYPE: PRT
<213> ORGANISM: Artificial Sequence
<220> FEATURE:
<223> OTHER INFORMATION: FG motif, Design 1

<400> SEQUENCE: 7

Gly Val His Val Pro Phe Thr Val Thr His Pro His Leu Pro Arg Ala
1               5                   10                  15

Leu Ser Ser His Leu Gln Phe Asn Lys Asp Gln Glu Ile Leu Phe Glu
                20                  25                  30

Gln Leu Ala Lys Lys Val Met Arg Val Leu Lys Glu Gln Leu Gly Ile
        35                  40                  45

Asp Glu Glu Glu Ala Arg Arg Ala Lys Gln Val Ser Phe Ile Val Tyr
50                  55                  60

Phe Lys Asp Gly Ser Ser Thr Lys Ile Asp Gly Ser Ser Asp Glu His
65                  70                  75                  80

Glu Glu Asn Lys Ile Asn Ala Ala Glu Ile Lys Lys Ile Glu Val Lys
                85                  90                  95

Val Asp

<210> SEQ ID NO 8
<211> LENGTH: 97
<212> TYPE: PRT
<213> ORGANISM: Artificial Sequence
<220> FEATURE:
<223> OTHER INFORMATION: FG motif, Design 2.

<400> SEQUENCE: 8

Gly Val Gln Val Pro Phe Thr Val Thr His Pro His Leu Pro Arg Ala
1               5                   10                  15

Leu Ser Ser His Leu Thr Phe Asn Lys Asp Gln Glu Ile Leu Tyr Glu
                20                  25                  30

Glu Leu Ala Lys Lys Val Met Arg Val Leu Glu Glu Gln Leu Gly Ile
        35                  40                  45

Thr Glu Glu Glu Ala Arg Arg Ala Lys Gln Val Lys Phe Trp Tyr Phe
        50                  55                  60

Lys Asp Gly Ser Ser Thr Glu Ile Asp Gly Ser Ser Asp Glu His Glu
65                  70                  75                  80

Glu Asn Lys Ile Asn Ala Ala Glu Ile Lys Lys Ile Glu Val Lys Val 85                  90                  95
Asp

<210> SEQ ID NO 9
<211> LENGTH: 98
<212> TYPE: PRT
<213> ORGANISM: Artificial Sequence
<220> FEATURE:
<223> OTHER INFORMATION: FG motif, Design 3

<400> SEQUENCE: 9

Gly Val Gln Val Pro Tyr Thr Val Thr His Pro His Leu Pro Arg Ala
1               5                   10                  15

Leu Ser Ser His Leu Thr Phe Asn Lys Asp Gln Glu Ile Leu Tyr Glu
            20                  25                  30

Gln Leu Ala Lys Lys Val Met Lys Val Ala Glu Lys Leu Gly Ile
        35                  40                  45

Thr Glu Glu Glu Ala Arg Arg Ala Lys Gln Phe Lys Phe Val Val Tyr
    50                  55                  60

Phe Lys Asp Gly Ser Ser Thr Glu Ile Asp Gly Lys Ser Asp Glu His
65                  70                  75                  80

Glu Glu Asn Lys Ile Asn Ala Ala Glu Ile Lys Lys Ile Glu Val Lys
                85                  90                  95

Ile Asp

<210> SEQ ID NO 10
<211> LENGTH: 98
<212> TYPE: PRT
<213> ORGANISM: Artificial Sequence
<220> FEATURE:
<223> OTHER INFORMATION: FG motif, Design 4

<400> SEQUENCE: 10

Gly Val Thr Val Pro Tyr Thr Val Thr His Pro His Leu Pro Arg Ala
1               5                   10                  15

Leu Ser Ser His Leu Thr Phe Asn Lys Asp Gln Glu Ile Leu Tyr Glu
            20                  25                  30

Gln Leu Ala Lys Lys Val Met Lys Val Leu Glu Lys Gln Leu Gly Ile
        35                  40                  45

Ser Glu Glu Glu Ala Arg Arg Ala Lys Gln Val Lys Phe Val Val Tyr
    50                  55                  60

Phe Lys Asp Gly Ser Ser Thr Glu Ile Asp Gly Ser Ser Asp Glu His
65                  70                  75                  80

Glu Glu Asn Lys Ile Asn Ala Ala Glu Ile Lys Lys Ile Glu Val Lys
                85                  90                  95

Val Asp

<210> SEQ ID NO 11
<211> LENGTH: 98
<212> TYPE: PRT
<213> ORGANISM: Artificial Sequence
<220> FEATURE:
<223> OTHER INFORMATION: FG motif, Design 5

<400> SEQUENCE: 11

Gly Val Thr Val Pro Phe Thr Val Thr His Pro His Leu Pro Arg Ala
1               5                   10                  15

Leu Lys Ser Glu Leu Thr Phe Lys Lys Asp Gln Glu Ile Leu Phe Glu
            20                  25                  30

His Leu Ala Ala Glu Val Lys Arg Val Leu Glu Glu Lys Gln Gly Ile
                35                  40                  45

Thr Glu Glu Glu Ala Lys Arg Ala Lys Gln Val Lys Phe Val Val Tyr
        50                  55                  60

Phe Lys Asp Gly Ser Ser Lys Glu Ile Asp Gly Ser Ser Ser Glu His
65                  70                  75                  80

Glu Gln Arg Lys Ile Asn Ala Ala Glu Ile Lys Lys Ile Glu Val Lys
                85                  90                  95

Ile Asp

<210> SEQ ID NO 12
<211> LENGTH: 98
<212> TYPE: PRT
<213> ORGANISM: Artificial Sequence
<220> FEATURE:
<223> OTHER INFORMATION: FG motif, Design 6.

<400> SEQUENCE: 12

Gly Thr Lys Val Pro Tyr Glu Val Thr His Pro His Leu Pro Arg Ala
1               5                   10                  15

Leu His Ser His Leu Glu Phe Glu Lys Asp Lys Glu Ile Leu Phe Glu
                20                  25                  30

His Leu Ala Lys Lys Val Lys Glu Val Leu Lys Glu Arg Gly Ile
                35                  40                  45

Ser Glu Glu Glu Ala Arg Arg Ala Lys Gln Val Lys Phe Val Val Tyr
        50                  55                  60

Phe Lys Asp Gly Ser Ser Gln Glu Ile Asp Gly Ser Ser Asp Glu Ser
65                  70                  75                  80

Lys Asp Asn Lys Ile Asn Ala Ala Glu Ile Lys Lys Ile Ser Val Asn
                85                  90                  95

Val Asp

<210> SEQ ID NO 13
<211> LENGTH: 98
<212> TYPE: PRT
<213> ORGANISM: Artificial Sequence
<220> FEATURE:
<223> OTHER INFORMATION: FG motif, Design 7

<400> SEQUENCE: 13

Gly Thr His Val Pro Phe Thr Val Thr His Pro His Leu Pro Arg Ala
1               5                   10                  15

Leu Ser Asp His Leu Glu Tyr Glu Lys Asp Lys Arg Val Leu Leu Glu
                20                  25                  30

Glu Ile Ala Lys Lys Val Lys Glu Val Leu Lys Lys Arg Gly Ile
                35                  40                  45

Ser Glu Glu Glu Ala Arg Arg Ala Lys Gln Val Ser Phe Ile Ile Phe
        50                  55                  60

Phe Lys Asp Gly Ser Ser Lys Lys Val Asp Gly Ser Ser Asp Glu Ser
65                  70                  75                  80

Lys Arg Asp Glu Val Asp Ala Ala Lys Ile Lys Lys Ile Glu Ile Asn
                85                  90                  95

Val Asp

<210> SEQ ID NO 14
<211> LENGTH: 98
<212> TYPE: PRT

```
<213> ORGANISM: Artificial Sequence
<220> FEATURE:
<223> OTHER INFORMATION: FG motif, Design 8

<400> SEQUENCE: 14

Gly Thr Arg Val Pro Phe Lys Val Thr His Pro His Leu Pro Arg Ala
1               5                   10                  15

Leu Glu Ser Glu Leu Glu Phe Glu Lys Asp Lys Glu Ile Leu Phe Glu
            20                  25                  30

Glu Leu Ala Lys Lys Val Lys Glu Met Ala Lys Lys Gln Arg Gly Ile
        35                  40                  45

Ser Glu Glu Glu Ala Arg Arg Ala Lys Gln Phe Lys Phe Ile Val Tyr
    50                  55                  60

Phe Lys Asp Gly Ser Ser Gln Glu Ile Asp Gly Lys Ser Asp Glu Ser
65                  70                  75                  80

Glu Asp Asn Lys Ile Asn Ala Ala Glu Ile Lys Lys Ile Glu Val His
                85                  90                  95

Val Asp

<210> SEQ ID NO 15
<211> LENGTH: 98
<212> TYPE: PRT
<213> ORGANISM: Artificial Sequence
<220> FEATURE:
<223> OTHER INFORMATION: FG motif, Design 9

<400> SEQUENCE: 15

Gly Thr Thr Val Pro Phe Thr Val Thr His Pro His Leu Pro Arg Ala
1               5                   10                  15

Leu Ser Ser Glu Leu Glu Phe Glu Lys Asp Lys Glu Ile Leu Phe Glu
            20                  25                  30

Glu Leu Leu Lys Lys Val Lys Glu Met Leu Lys Lys Gln Arg Gly Ile
        35                  40                  45

Ser Glu Glu Glu Ala Arg Arg Ala Lys Gln Val Lys Phe Ile Val Tyr
    50                  55                  60

Phe Lys Asp Gly Ser Ser Gln Glu Ile Asp Gly Ser Ser Asp Glu His
65                  70                  75                  80

Lys Glu Asn Lys Ile Asn Ala Ala Glu Ile Lys Lys Ile Glu Val His
                85                  90                  95

Val Asp

<210> SEQ ID NO 16
<211> LENGTH: 97
<212> TYPE: PRT
<213> ORGANISM: Artificial Sequence
<220> FEATURE:
<223> OTHER INFORMATION: FG motif, Design 10

<400> SEQUENCE: 16

Gly Thr Thr Val Pro Phe His Val Thr His Pro His Leu Pro Arg Ala
1               5                   10                  15

Leu Gln Ser Glu Leu Glu Phe Glu Lys Asp Lys Glu Ile Leu Leu Glu
            20                  25                  30

His Leu Ala Lys Lys Val Lys Glu Val Leu Lys Lys Gln Arg Gly Ile
        35                  40                  45

Ser Glu Glu Glu Ala Lys Arg Ala Lys Gln Val Lys Phe Trp Tyr Phe
    50                  55                  60

Lys Asp Gly Ser Ser Lys Glu Val Asp Gly Ser Ser Glu Glu Ser Glu
```

```
                65                  70                  75                  80
Asp Asp Lys Ile Asn Ala Ala Glu Ile Lys Lys Ile Ser Val Asn Val
                    85                  90                  95

Asp

<210> SEQ ID NO 17
<211> LENGTH: 140
<212> TYPE: PRT
<213> ORGANISM: Homo sapiens
<220> FEATURE:
<221> NAME/KEY: MISC_FEATURE
<222> LOCATION: (1)..(140)
<223> OTHER INFORMATION: Chain A, Signal transducing adapter molecule 1;
      PDB: 3LDZ_A

<400> SEQUENCE: 17

Phe Ala Thr Asn Pro Phe Asp Gln Asp Val Glu Lys Ala Thr Ser Glu
1               5                   10                  15

Met Asn Thr Ala Glu Asp Trp Gly Leu Ile Leu Asp Ile Cys Asp Lys
                20                  25                  30

Val Gly Gln Ser Arg Thr Gly Pro Lys Asp Cys Leu Arg Ser Ile Met
            35                  40                  45

Arg Arg Val Asn His Lys Asp Pro His Val Ala Met Gln Ala Leu Thr
    50                  55                  60

Leu Leu Gly Ala Cys Val Ser Asn Cys Gly Lys Ile Phe His Leu Glu
65                  70                  75                  80

Val Cys Ser Arg Asp Phe Ala Ser Glu Val Ser Asn Val Leu Asn Lys
                85                  90                  95

Gly His Pro Lys Val Cys Glu Lys Leu Lys Ala Leu Met Val Glu Trp
            100                 105                 110

Thr Asp Glu Phe Lys Asn Asp Pro Gln Leu Ser Leu Ile Ser Ala Met
        115                 120                 125

Ile Lys Asn Leu Lys Glu Gln Gly Val Thr Phe Pro
    130                 135                 140

<210> SEQ ID NO 18

<400> SEQUENCE: 18

000

<210> SEQ ID NO 19
<211> LENGTH: 96
<212> TYPE: PRT
<213> ORGANISM: Cupriavidus pinatubonensis JMP134
<220> FEATURE:
<221> NAME/KEY: MISC_FEATURE
<222> LOCATION: (1)..(96)
<223> OTHER INFORMATION: Chain B, phenylacetate-CoA oxygenase subunit
      PaaB; PDB: 3EGR_B
<220> FEATURE:
<221> NAME/KEY: MISC_FEATURE
<222> LOCATION: (2)..(2)
<223> OTHER INFORMATION: Xaa is any amino acid.
<220> FEATURE:
<221> NAME/KEY: MISC_FEATURE
<222> LOCATION: (39)..(39)
<223> OTHER INFORMATION: Xaa is any amino acid
<220> FEATURE:
<221> NAME/KEY: MISC_FEATURE
<222> LOCATION: (76)..(76)
<223> OTHER INFORMATION: Xaa is any amino acid.
<220> FEATURE:
<221> NAME/KEY: MISC_FEATURE
<222> LOCATION: (96)..(96)
```

<223> OTHER INFORMATION: Xaa is any amino acid.

<400> SEQUENCE: 19

```
Gly Xaa Thr Gln Lys Glu Trp Pro Leu Trp Glu Val Phe Val Arg Ser
1               5                   10                  15

Lys Gln Gly Leu Glu His Lys His Cys Gly Ser Leu His Ala Thr Asp
                20                  25                  30

Ala Gln Gln Ala Leu His Xaa Ala Arg Asp Val Tyr Thr Arg Arg Gln
            35                  40                  45

Glu Gly Val Ser Ile Trp Val Val Pro Ser Thr Ala Ile Thr Ala Ser
    50                  55                  60

Ala Pro Glu Glu Lys Pro Glu Leu Phe Asp Pro Xaa Ala Asp Lys Ile
65                  70                  75                  80

Tyr Arg His Pro Thr Phe Tyr Gln Leu Pro Asp Glu Val Asn His Xaa
                85                  90                  95
```

<210> SEQ ID NO 20

<400> SEQUENCE: 20

000

<210> SEQ ID NO 21
<211> LENGTH: 102
<212> TYPE: PRT
<213> ORGANISM: Mycobacterium smegmatis str. MC2 155
<220> FEATURE:
<221> NAME/KEY: MISC_FEATURE
<222> LOCATION: (1)..(102)
<223> OTHER INFORMATION: Chain B, Low Molecular Weight Protein Antigen
      7; PDB: 3Q4H_B
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid.
<220> FEATURE:
<221> NAME/KEY: MISC_FEATURE
<222> LOCATION: (11)..(11)
<223> OTHER INFORMATION: Xaa is any amino acid.
<220> FEATURE:
<221> NAME/KEY: MISC_FEATURE
<222> LOCATION: (18)..(18)
<223> OTHER INFORMATION: Xaa is any amino acid.
<220> FEATURE:
<221> NAME/KEY: MISC_FEATURE
<222> LOCATION: (44)..(51)
<223> OTHER INFORMATION: Residues replaced by those of the R loop.
<220> FEATURE:
<221> NAME/KEY: MISC_FEATURE
<222> LOCATION: (49)..(49)
<223> OTHER INFORMATION: Xaa is any amino acid.
<220> FEATURE:
<221> NAME/KEY: MISC_FEATURE
<222> LOCATION: (62)..(62)
<223> OTHER INFORMATION: Xaa is any amino acid.
<220> FEATURE:
<221> NAME/KEY: MISC_FEATURE
<222> LOCATION: (72)..(72)
<223> OTHER INFORMATION: Xaa is any amino acid.
<220> FEATURE:
<221> NAME/KEY: MISC_FEATURE
<222> LOCATION: (81)..(81)
<223> OTHER INFORMATION: Xaa is any amino acid.
<220> FEATURE:
<221> NAME/KEY: MISC_FEATURE
<222> LOCATION: (83)..(83)
<223> OTHER INFORMATION: Xaa is any amino acid.

```
<400> SEQUENCE: 21

Xaa Ser Gln Ile Xaa Tyr Asn Tyr Pro Ala Xaa Leu Ala His Ala Ala
1               5                   10                  15

Glu Xaa Asn Thr Tyr Ser Gly Ala Leu His Ala Val Gly Ala Asp Ile
            20                  25                  30

Ala Ala Glu Gln His Ala Leu Ala Ser Ala Trp Gln Gly Asp Thr Gly
        35                  40                  45

Xaa Thr Tyr Gln Ala Trp Gln Ala Gln Trp Asn Gln Ala Xaa Glu Glu
    50                  55                  60

Leu Val Arg Ala Tyr Arg Ala Xaa Ala Thr Thr His Glu Gln Asn Thr
65                  70                  75                  80

Xaa Ala Xaa Ser Ala Arg Asp Gln Ala Glu Gly Ala Lys Trp Gly Thr
                85                  90                  95

His His His His His His
                100

<210> SEQ ID NO 22

<400> SEQUENCE: 22

000

<210> SEQ ID NO 23
<211> LENGTH: 8
<212> TYPE: PRT
<213> ORGANISM: Homo sapiens

<400> SEQUENCE: 23

Gln Gly Asp Thr Gly Met Thr Tyr
1               5

<210> SEQ ID NO 24
<211> LENGTH: 10
<212> TYPE: PRT
<213> ORGANISM: Homo sapiens

<400> SEQUENCE: 24

Ala Thr Ser Glu Met Asn Thr Ala Glu Asp
1               5                   10

<210> SEQ ID NO 25
<211> LENGTH: 10
<212> TYPE: PRT
<213> ORGANISM: Cupriavidus pinatubonensis (strain JMP 134 / LMG 1197)

<400> SEQUENCE: 25

Val Arg Ser Lys Gln Gly Leu Glu His Lys
1               5                   10
```

PAN-ANTIALLERGY VACCINE

STATEMENT OF ACKNOWLEDGMENT

The inventors thank the High Performance Computing Centre at King Abdulaziz University for making available the Aziz high performance computer used to perform the necessary computations.

REFERENCE TO A SEQUENCE LISTING

In accordance with 37 CFR § 1.52(e)(5), the present specification makes reference to a Sequence Listing (submitted electronically as a .txt file named "526195US_ST25.txt". The .txt file was generated on Nov. 10, 2020 and is 21.1 in size. The entire contents of the Sequence Listing are herein incorporated by reference.

BACKGROUND OF THE INVENTION

Field of the Invention

The invention pertains to the fields of immunology and molecular biology and more specifically to a pan-allergy vaccine and a method for identifying its structure.

Description of the Related Art

The condition "allergy" was first defined by Clemens von Pirquet in 1906 when he discovered that second injections of horse serum caused a severe inflammatory reaction in some individuals, but not all. He termed this condition allergy, from the Greek words allos "other" and ergon "works" and called an allergy causing agent an "allergen"; C. Von Pirquet. 1909. Allergie. Monchener Medizinische Wochenschrift.

In the 1960s Kimishige Ishizaka and Teruko Ishizaka demonstrated that allergic reactions were mediated by a new class of antibodies that they had discovered and called immunoglobulin E or IgE. See M. Chapman. 1998. Allergens. Encyclopedia of Immunology; and Ishizaka, K., et al. 1966. *Physico-chemical properties of human reaginic antibody. IV. Presence of a unique immunoglobulin as a carrier of reaginic activity*. J Immunol 97: 75-85. IgE is now recognized as one of the five major isotypes of human antibodies: IgA, IgD, IgE, IgG, and IgM.

Unlike IgM and IgG, which provide the primary and secondary response to foreign antigens, such viral or bacterial antigens, IgE binds to mast cells and basophils and is associated with allergy and with antiparasitic immunity. IgE plays an important role in resistance to parasites which unlike viruses and bacteria, but like human are eukaryotes as are other mammals like pet cats, dogs and pollen producing plants. Unfortunately, IgE can target innocuous foreign substances that look like parasites but are not usually harmful such as cat dander, shrimp, and pollen, leading to a type of inflammatory reaction termed an allergic reaction and known medically as type I hypersensitivity.

IgE binds to high affinity IgE receptor (FcεRI) on mast cells and mediates allergy and antiparasitic immunity in part via histamine released by mast cells. Thus, it is not surprising that allergy is often treated with antihistamine drugs.

IgE mediated allergic response have diverse manifestations which can range from mild to severe and life threatening. Humans as well as dogs, horses and other mammals are known to suffer the clinical symptoms of IgE-mediated type I hypersensitivity responses. In their most serious manifestation these IgE-mediated allergic responses cause serious asthma or even life-threatening anaphylactic shock. Reports of an increase in the number of individuals suffering from allergic manifestations began in the second half of the last century and the incidence of allergy has now reached pandemic proportions; Pawankar, R., et al., 2011. World Allergy Organization (WAO) white book on allergy. Wisconsin: World Allergy Organisation.

One of the perceived reasons for the continual increase in allergy incidence, especially in the developed world, is a hypothesis termed the Hygiene Hypothesis, originally formulated by Strachan, it states that a lack of exposure to infectious pathogens in early childhood, i.e. living in too clean of an environment, can lead to inadequate immune system development, i.e. a shift from the $Th_1$ immune response (bacteria, viruses) to that of the $Th_2$ immune response (parasite, allergy), resulting in an increase in susceptibility to develop allergy. See Strachan, D. P. 1989. *Hay fever, hygiene, and household size*. Bmj 299: 1259-60; Strachan, D. P. 2000. *Family size, infection and atopy: the first decade of the "hygiene hypothesis"*. Thorax 55 Suppl 1:S2-10; and Okada, H., Kuhn, C., Feillet, H. & Bach, J. F. 2010. *The 'hygiene hypothesis' for autoimmune and allergic diseases: an update*. Clin Exp Immunol 160: 19. doi: 10.1111/j.1365-2249.2010.04139.x. Further studies into this immunological pathway have shed light into the viability of this hypothesis and showed a correlation between tuberculosis infections in childhood and lack of allergy in adulthood. See von Hertzen, L., et al. 1999. *Mycobacterium tuberculosis infection and the subsequent development of asthma and allergic conditions*. J Allergy Clin Immunol 104: 1211-1214.

Pharmacotherapy or therapy with antihistamines, corticosteroids, epinephrine, and other drugs, is the most widely used passive treatment for allergy. Such drugs alleviate the symptoms of allergy without curing its underlying cause. Passive immunotherapeutic strategies that do not expose a patient to an allergen have met with some success. These passive strategies involve administering non-anaphylactogenic antibodies which have demonstrated their capacity to treat type I hypersensitivity responses. Humanized mouse monoclonal antibodies, such as Omalizumab, have been successfully used to treat allergy, but are also associated with a number of drawbacks including poor effectiveness in obese patients, complicated logistics, high cost, and provision of only a temporary reduction in allergy symptoms; Presta, L. G., et al. 1993. *Humanization of an antibody directed against IgE*. J Immunol 151: 2623-32.

In spite of extensive worldwide research efforts, no effective active therapeutic intervention strategies (as opposed to passive drug therapies) are currently available. The quest to actively treat allergy is not a new concept, it was first attempted in 1911 by Noon, in which subcutaneous injections of an allergen extract were administered in an effort to desensitize atopic patients to the allergen as a form of homeopathy. See L. Noon. 1911. *Prophylactic Inoculation Against Hay Fever*. The Lancet 177: 1572-1573. While this form of treatment was successful in treating some allergies such as anaphylaxis and allergic rhinitis, it was unsuccessful in treating asthma. See Lewis, D. B. 2002. *Allergy immunotherapy and inhibition of Th2 immune responses: a sufficient strategy?*. Curr Opin Immunol 14: 644-51. Sublingual immunotherapy is currently being researched where allergen extracts are placed under the tongues of patients to expose them to allergens in hope of desensitizing allergic responses. See Gidaro, G. B., et al. 2005. *The safety of sublingual-swallow immunotherapy: an analysis of published studies*.

Clin Exp Allergy 35: 565-71. doi: 10.1111/j. 1365-2222.2005.02240.x. However, the efficacy of these allergen-based active immunotherapies varies greatly depending on genetics and other background of the patient and on the nature of the particular allergen and mode of exposure to the allergen. Moreover, Allergen-based active immunization risks aggravating the allergic symptoms in a patient by further sensitizing a patient to an allergen; Moverare, R., et al. 2002. *Development of new IgE specificities to allergenic components in birch pollen extract during specific immunotherapy studied with immunoblotting and Pharmacia CAP System*. Allergy 57: 423-30. Consequently a standard and safe protocol generally applicable to a wide-range of patients has not been developed.

In view of the drawbacks of drug treatment, passive immunological treatment, and allergen-based active treatment of allergy, the inventors sought to develop a new mode of active immunological treatment of allergy that eliminates the risk of further sensitizing a patient to harmful allergens, which did not require passive administration of drugs or antibodies, and which was generally useful for a variety of different patients with different allergies. As disclosed herein, the inventors focused their efforts on development of a new active immunotherapeutic strategy that primes the immune system against its own allergy-inducing IgE antibodies thus neutralizing them and reducing the severity of allergy.

SUMMARY OF THE INVENTION

In one aspect the present disclosure includes an active immunization strategy and vaccine that do not rely on use of a particular allergen, but rather actively immunizes a subject or patient against the IgE which mediates many allergic phenomena. The active immunization strategy of the invention can act as a pan-anti-allergy vaccine because it targets the common factor in IgE-mediated allergic responses—IgE—rather than an individual allergen. This pan-anti-allergy vaccine comprises an engineered protein construct comprising a scaffold protein into which an IgE motif segment has been inserted.

Another aspect the present disclosure includes computationally designing and engineering the protein construct by excising the motif of interest from the IgE structure and grafting it into several different scaffold protein structures. The conformational features of each of the various scaffold protein structures were then evaluated with the objective of obtaining an immunogen that would efficiently induce antibodies against IgE. One specific preferred scaffold protein structure is a *Staphylococcus* extracellular adherence protein that comprises ITVNGTSQNI (SEQ ID NO: 6) into which epitopes of the FG loop of IgE can be inserted. The inventors have found that this construct displayed the IgE motif of interest in substantially its original three dimensional form without any of the surrounding native IgE structure. This permits the immune system of an immunized allergy patient to target that IgE motif only. A brief summary of this strategy is provided by FIG. 1.

Another aspect the present disclosure includes is directed to immunogenic or vaccinogenic compositions comprising this protein construct, a DNA-based vaccine which expresses the protein construct when administered to a subject, as well as to methods for treating allergic diseases, disorders and conditions using such immunogens or vaccines.

Another aspect of the invention is directed to a computer-based method for designing and evaluating protein constructs presenting IgE epitopes or determinants, such as the FG loop and to methods for expressing and purifying the resulting protein constructs.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

FIGS. 4A-4C illustrate three structures that successfully grafted the FG loop 3LDZ chain A (FIG. 4A); 1YN3 chain A (FIG. 4B); and 3EGR chain B (FIG. 4C). 1YN3 was chosen since the native structure was easily forward folded using AbinitioRelax as shown in FIG. 5. Thus it was easier to redesign this structure and it did result is a structure with a large energy gap between the desired structure and any other potential structure.

FIG. 5 illustrates an AbinitioRelax result of the native 1YN3 protein showing a successful simulation which describes a funnel shaped plot with the lowest simulated energy close to the predicted energy and RMSD of the structure.

FIG. 6A details the structure of the FG motif.

FIG. 6B details the structure of the 1YN3 scaffold protein before grafting the FG motif from IgE.

FIG. 6C details the structure of the 1YN3 scaffold after grafting the FG motif.

FIGS. 7A-7AD illustrate ten potential vaccine candidates that display the FG loop in its native three dimensional structures. Each structure is superimposed onto the lowest energy and RMSD structures from the AbinitioRelax simulation and the corresponding lowest RMSD value of the simulation, thus all structures were predicted to fold within a sub angstrom level of the designed structure. The corresponding amino acid sequences of Designs 1-10 depicted in these figures appear as SEQ ID NOS: 7 to 16. These figures also show the fragment quality used in each AbinitioRelax simulation and the AbinitioRelax plot showing a successful funnel shaped plot for all structures.

Figure 7A:
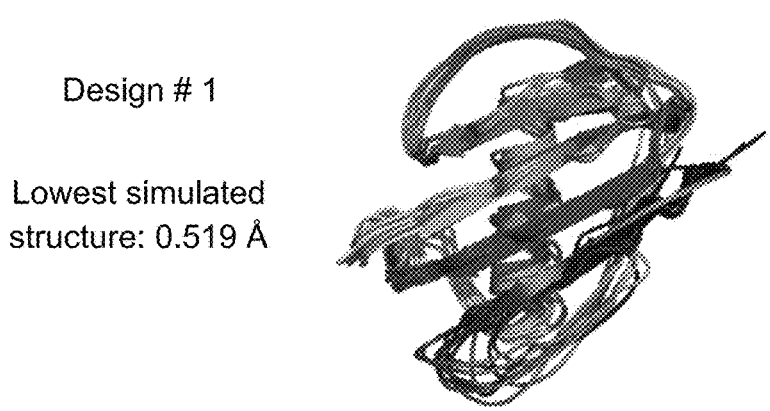
Figure 7B:
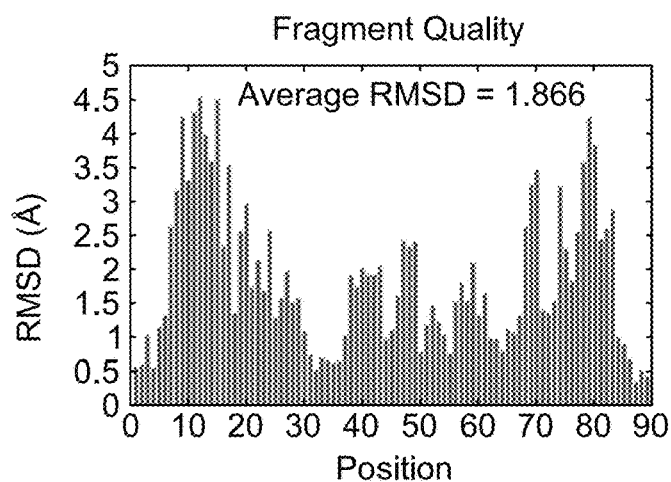
Figure 7C:
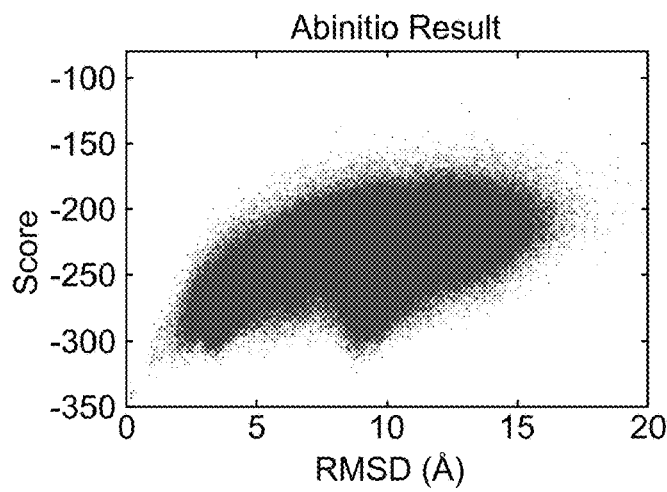

FIGS. 7A-7C characterize the peptide sequence of SEQ ID NO: 7 (Design 1) which appears at the end of FIG. 7C.

Figure 7D:
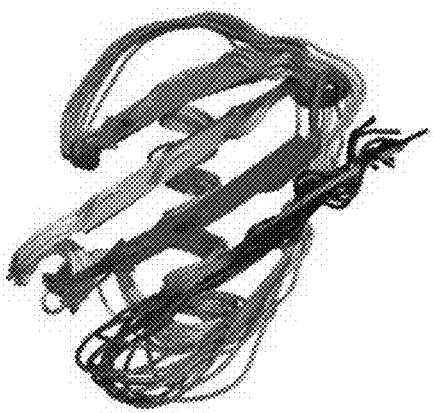
Figure 7E:
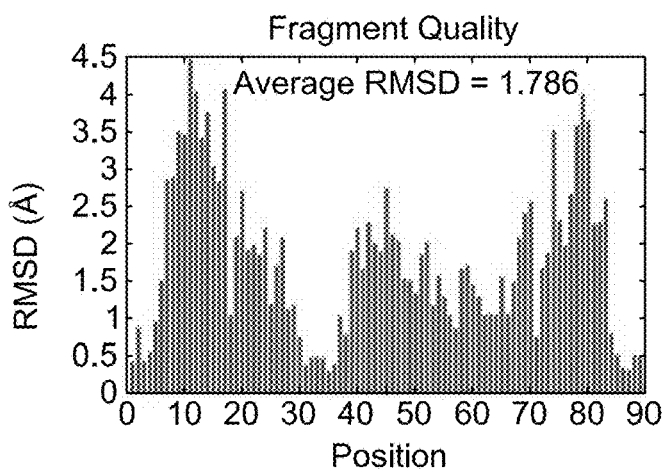
Figure 7F:
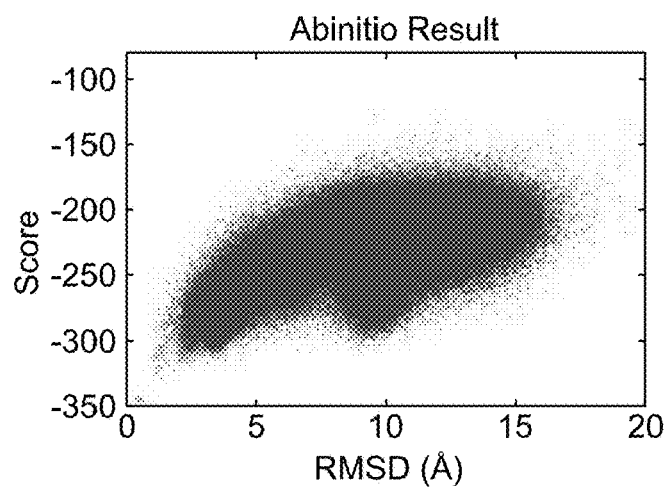

FIGS. 7D-7F characterize the peptide sequence of SEQ ID NO: 8 (Design 2) which appears at the end of FIG. 7F.

Figure 7G:
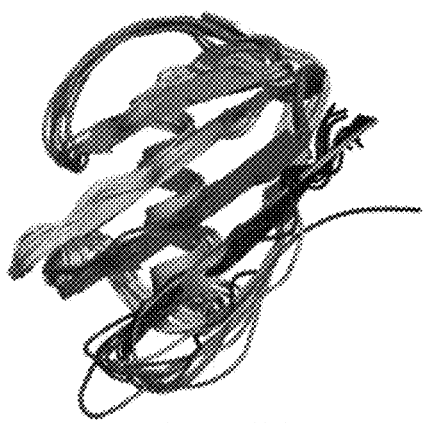
Figure 7H:
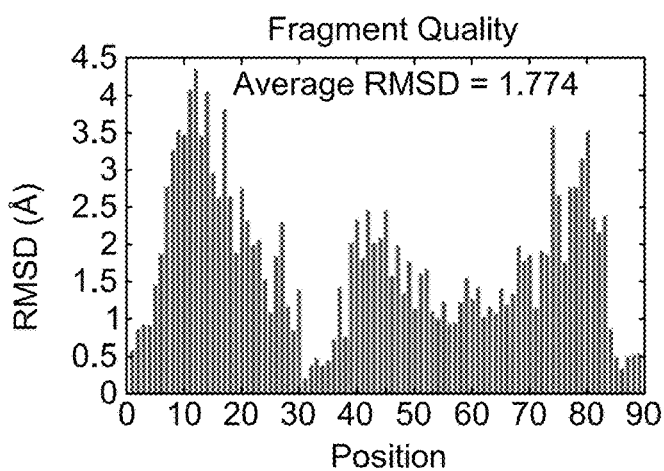
Figure 7I:
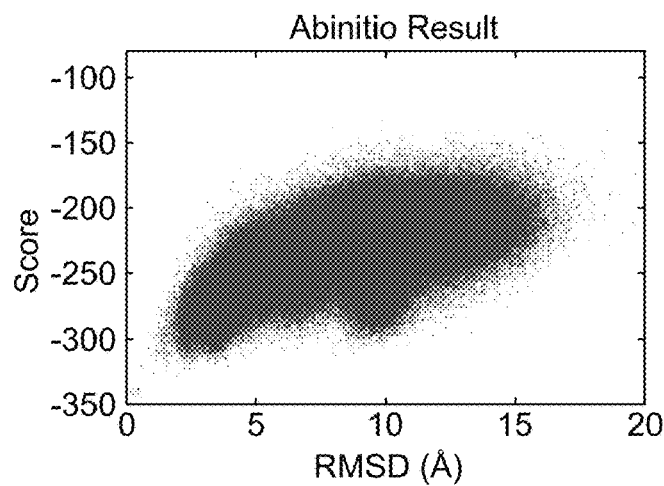

FIGS. 7G-7I characterize the peptide sequence of SEQ ID NO: 9 (Design 3) which appears at the end of FIG. 7I.

Figure 7J:
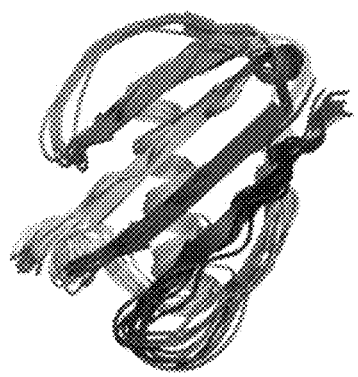
Figure 7K:
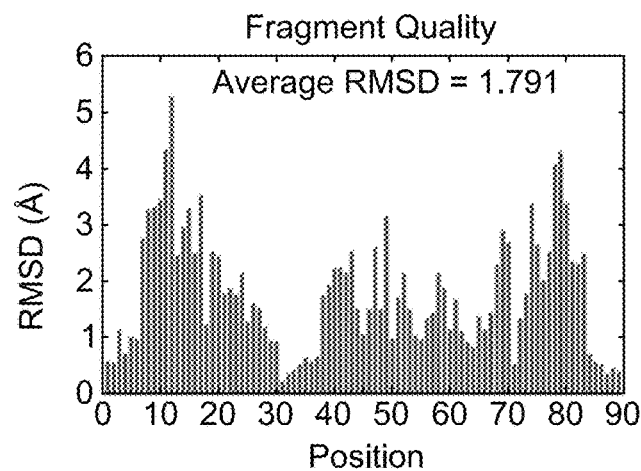
Figure 7L:
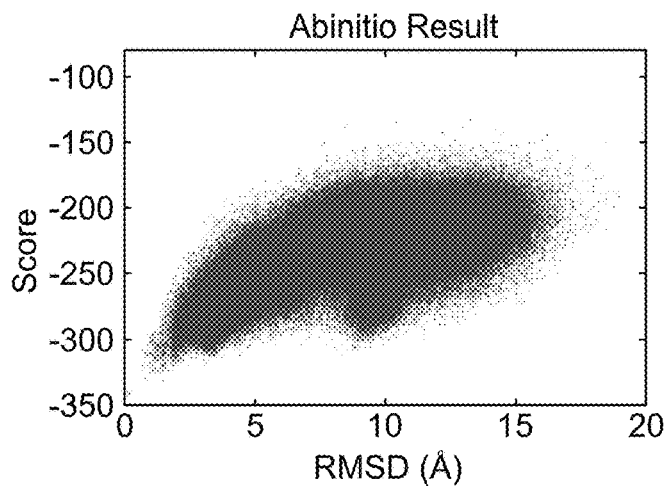

FIGS. 7J-7L characterize the peptide sequence of SEQ ID NO: 10 (Design 4) which appears at the end of FIG. 7L.

Figure 7M:
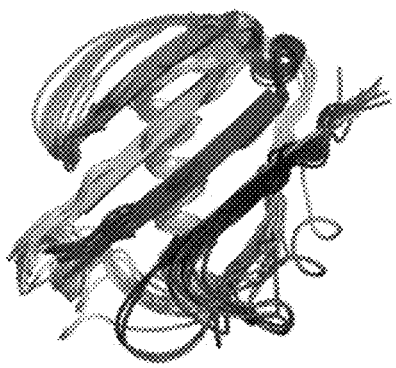
Figure 7N:
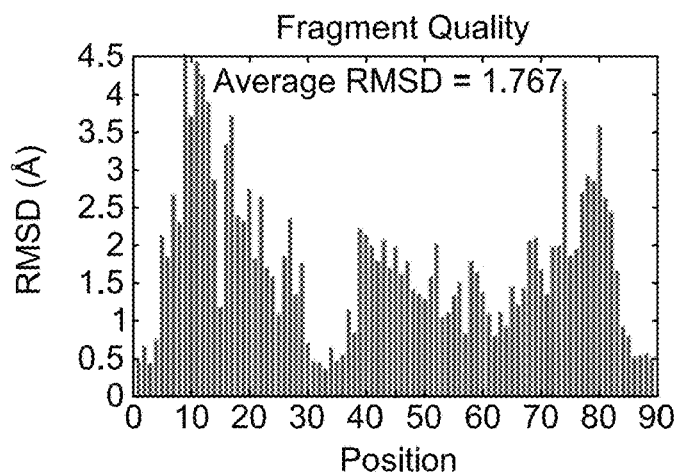
Figure 7O:
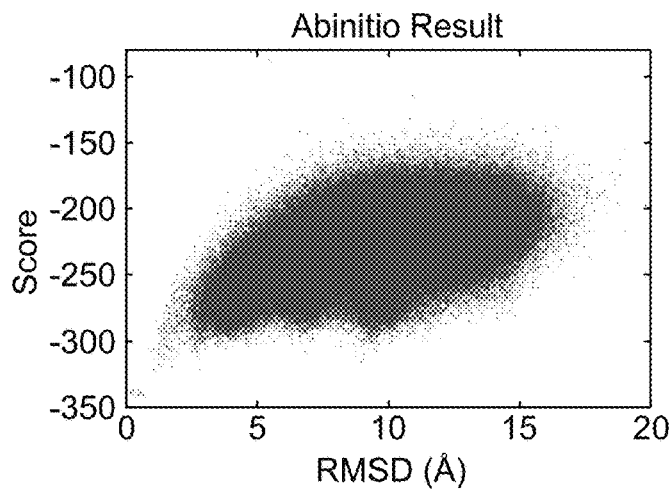

FIGS. 7M-7O characterize the peptide sequence of SEQ ID NO: 11 (Design 5) which appears at the end of FIG. 7O.

Figure 7P:
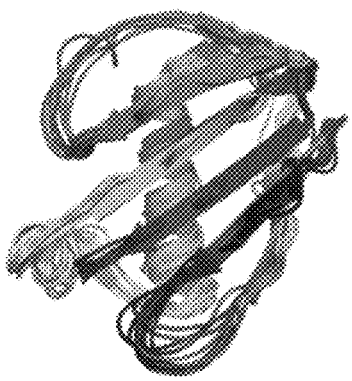
Figure 7Q:
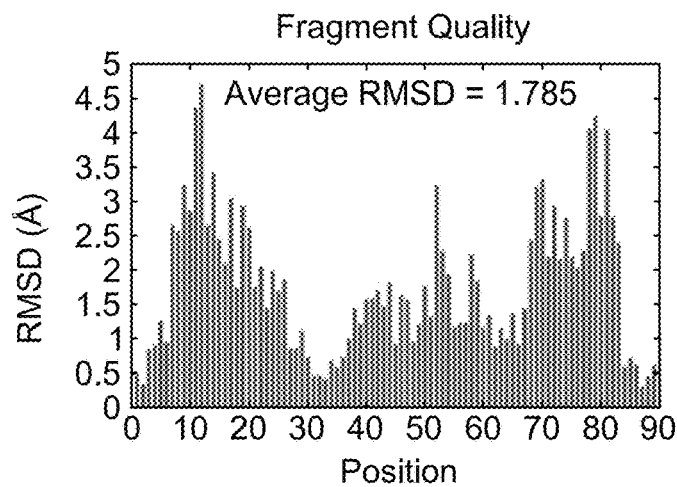
Figure 7R:
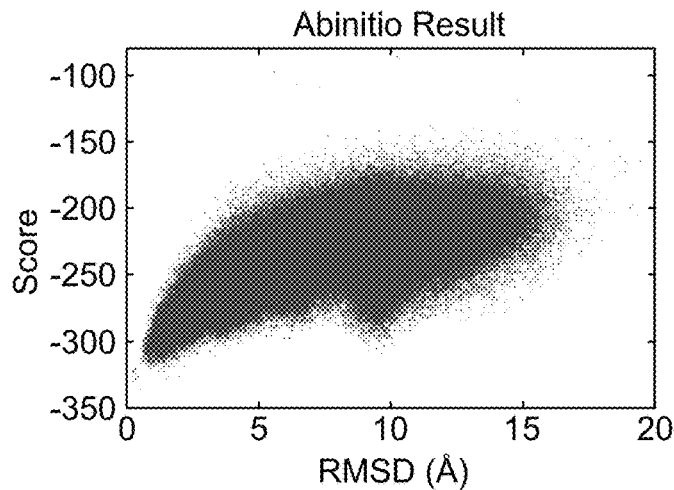

FIGS. 7P-7R characterize the peptide sequence of SEQ ID NO: 12 (Design 6) which appears at the end of FIG. 7R.

Figure 7S:
Figure 7T:
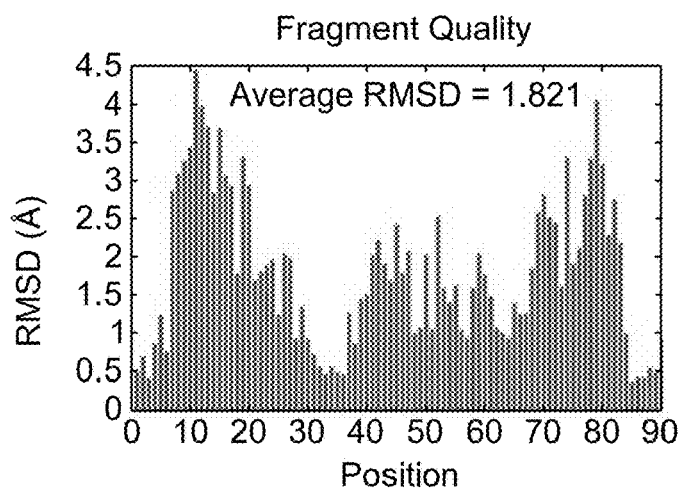
Figure 7U:
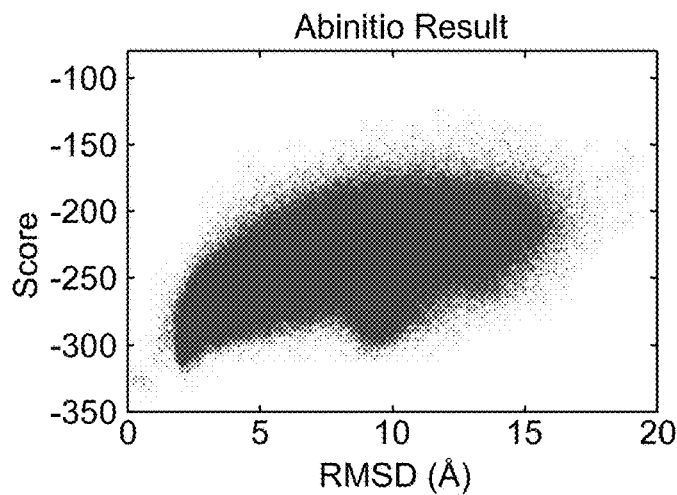

FIGS. 7S-7U characterize the peptide sequence of SEQ ID NO: 13 (Design 7) which appears at the end of FIG. 7U.

Figure 7V:
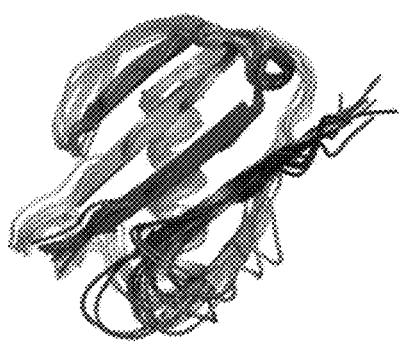
Figure 7W:
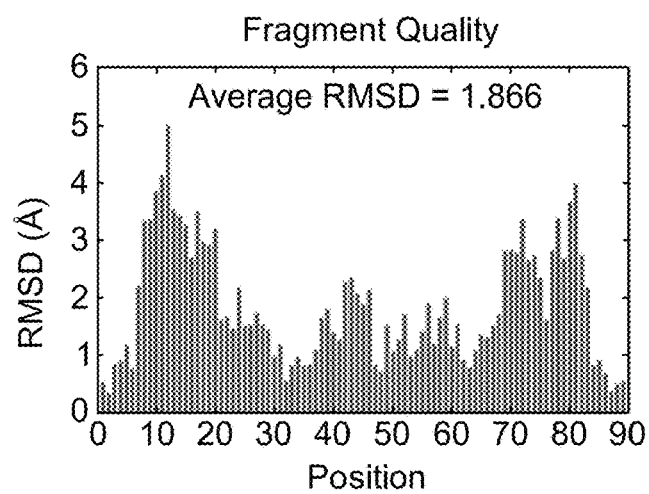
Figure 7X:
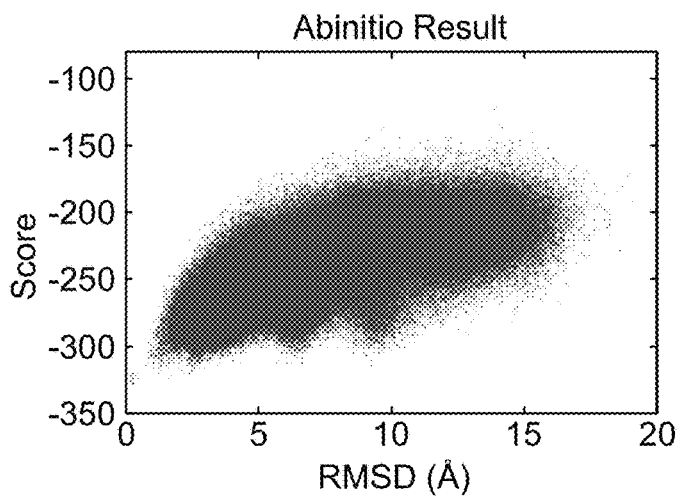

FIGS. 7V-7X characterize the peptide sequence of SEQ ID NO: 14 (Design 8) which appears at the end of FIG. 7X.

Figure 7Y:
Figure 7Z:
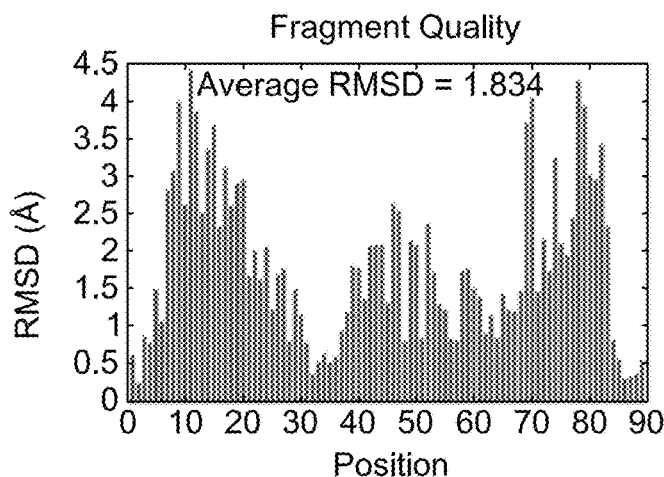
Figure 7A:
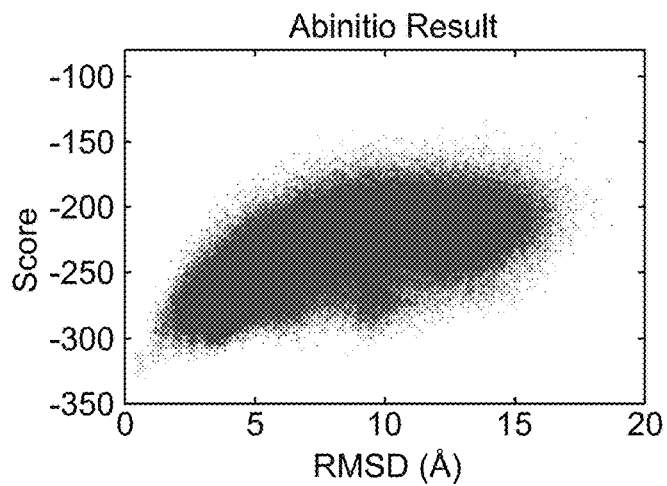
Figure 7A:
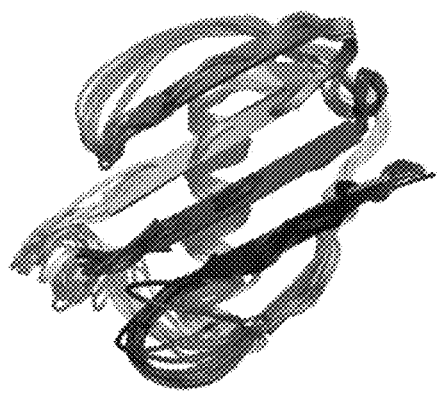
Figure 7A:
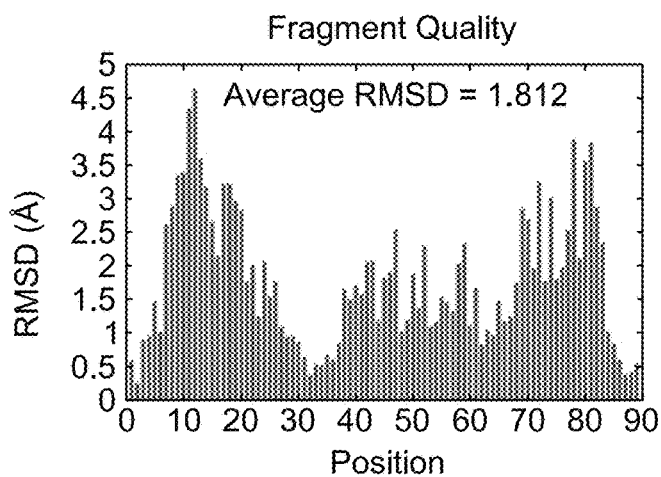
Figure 7A:
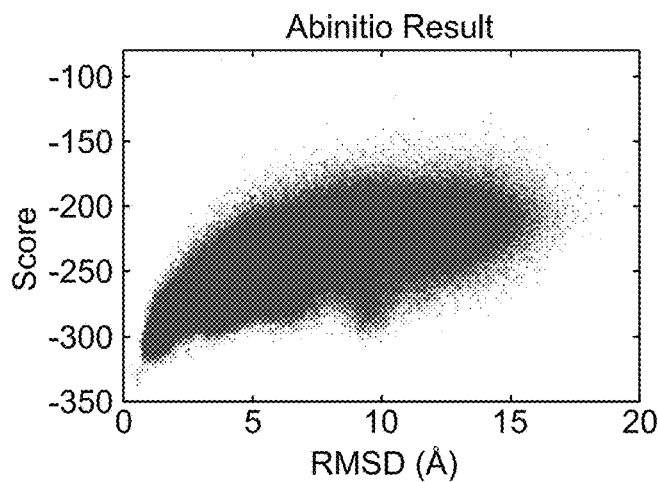

FIGS. 7Y-7AA characterize the peptide sequence of SEQ ID NO: 15 (Design 9) which appears at the end of FIG. 7AA.

FIGS. 7AB-7AD characterize the peptide sequence of SEQ ID NO: 16 (Design 10) which appears at the end of FIG. 7AD.

Figure 8:
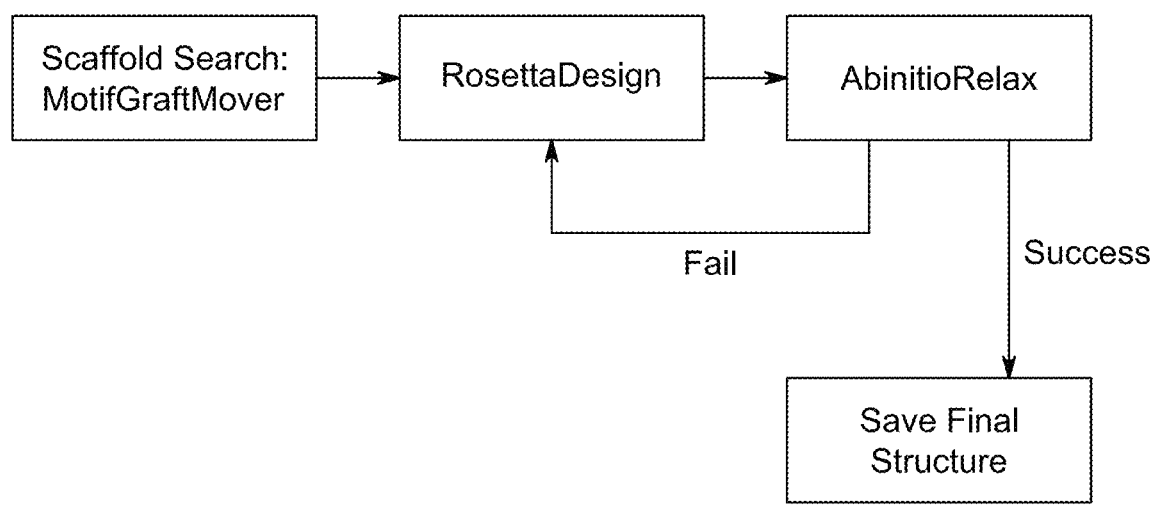

FIG. 8 is a flow chart showing some preferred steps used to design peptide structures.

DETAILED DESCRIPTION OF THE INVENTION

The description and specific examples below, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested. Embodiments of this technology include, but are not limited to the following.

One embodiment of the invention is directed to a protein construct comprising an IgE motif segment and a scaffold, preferably an exogenous non-human protein scaffold, into which the IgE motif segment is embedded. The scaffold holds the IgE segment in a conformation suitable for inducing an immune response against IgE. This protein construct may be used as an antigen, immunogen or vaccine to induce immune responses against the IgE motif segment. The induced anti-IgE immune responses reduce the severity of IgE mediated allergy and other immunological phenomena and thus may be used to treat a subject having a disease, disorder or condition associated with or mediated by IgE.

Another embodiment of the invention is directed to a protein construct comprising a scaffold segment and a motif segment. The scaffold segment is selected to present the motif segment which comprises T cell or B cell epitopes or determinants of IgE, especially of human IgE. Typically, the scaffold segment is a protein other than IgE or is exogenous to human IgE, or exogenous to humans. A protein construct may comprise the entire scaffold protein substituted with the IgE motif or active or epitopic fragments thereof, for example, a protein construct where immunologically non-essential amino acid sequences are removed.

A protein construct may also comprise a complex or conjugate containing the protein construct or an active fragment thereof, such as a larger chimeric or fusion protein, a bead or other substrate to which the protein construct is noncovalently or covalently bound, or a composition, such as an emulsion or liposome containing the protein construct or an immunogenically active fragment thereof capable of inducing antibodies that recognize the IgE motif.

Typically the scaffold segment is modified, by replacement of a scaffold subsegment with the amino acid residues comprising the IgE motif segment. In other words, the scaffold protein is modified by insertion or replacement of the amino acid residues of the IgE motif. In one embodiment, the motif comprises an IgE FG loop (SEQ ID NO: 2) or an IgE R loop (SEQ ID NO: 3) or epitopic portions thereof. However, other epitopes of IgE may be used instead of, or in addition to, the FG or R loop, such as the BC or DE loops, or epitopic portions thereof described by FIG. 2.

In one embodiment the protein construct as disclosed herein comprises a scaffold segment corresponding to an extracellular adherence protein ("EAP") domain of a member of the genus Staphylococcus, especially Staphylococcus aureus, that is at least 70, 75, 80, 85, 90, 91, 92, 93, 94, 95, 96, 97, 98, 99 or 100% identical to the EAP of SEQ ID NO: 5 or which has 1, 2, 3, 4, 5, 6, 7, 8, 9, 10, 11, 12, 13, 14, 15, 16, 17, 18, 19, 20 or >20 deletions, insertions, or substitutions of amino acid residues to the sequence of SEQ ID NO:5. In some preferred embodiments, the protein construct may comprise the extracellular adherence protein 1YN3 chain A (SEQ ID NO: 5) or a protein that is at least 90, 95 or 99% identical thereto.

Other scaffold proteins may be used in some embodiments such as scaffold proteins comprising 3LDZ chain A comprising SEQ ID NO: 17 or a protein that is at least 90-95% identical thereto; scaffolds comprising 3EGR chain A comprising SEQ ID NO: 19 or a protein that is at least 90-95% identical thereto; or scaffolds comprising 3Q4H chain B comprising SEQ ID NO: 21 or a protein that is at least 90-95% identical thereto. In the 3Q4H structure, residues QGDTGMTY (SEQ ID NO: 23) at positions 44-51 were replaced by the R motif; in the 3LDZ structure residues ATSEMNTAED (SEQ ID NO: 24) at positions 16-25 were replaced by the FG motif; and in the 3EGR structure residues VRSKQGLEHK (SEQ ID NO: 25) at positions 13-22 were replaced by the FG motif.

In some embodiments, the protein construct comprises an IgE motif segment comprising the FG loop described by SEQ ID NO: 2. For example, the IgE motif may comprise any one of the protein sequences described by SEQ ID NOS: 7 to 16 which each contain said FG loop.

In another embodiment, the IgE motif comprises an IgE R loop (SEQ ID NO: 3), BC loop, or DE loop segment in combination with a scaffold segment of the extracellular adherence protein 1YN3 chain A (SEQ ID NO: 5), 3LDZ (SEQ ID NO: 17) or 3EGR (SEQ ID NO: 19) or a protein that is at least 90, 95 or 100% identical thereto.

In some embodiments, the protein construct disclosed herein will comprise a variant scaffold protein or variant IgE motif, that can have 1, 2, 3, 4, 5, 6, 7, 8, 9, 10 or more deletions, insertions or substitutions of an amino acid residue of the scaffold or motif or have at least 70, 80, 90, 95, 99 or up to 100% sequence identity with a disclosed amino acid sequence, such as the IgE motif and scaffold proteins identified by sequence identifiers herein. BLASTP may be used to identify an amino acid sequence having at least 70%, 75%, 80%, 85%, 87.5%, 90%, 92.5%, 95%, 97.5%, 98%, 99% sequence similarity to a reference amino acid sequence, such as those described herein using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. Default settings for BLASTP are described by and incorporated by reference to http://blast.ncbi.nlm.nih.gov/Blast.cgi?PROGRAM=blastp&PAGE_TYPE=BlastSearch&LINK_LOC=blasthome (last accessed Jan. 9, 2020). This disclosure also encompasses degenerate polynucleotide sequences encoding the proteins disclosed herein which are deduced from the corresponding amino acid sequences using the genetic code.

Any scaffold protein that effectively presents the IgE epitopes in the IgE motif segment to a subject's immune system may be used. However, the inventors have discovered that only some protein constructs are capable of efficient presentation of IgE epitopes. Based on structural analysis, preferred scaffolds include the extracellular adherence protein 1YN3 chain A (SEQ ID NO: 5) or a protein that is at least 90, 95, 96, 97, 98, 99 or 100% identical thereto or a *Staphylococcus* extracellular adherence protein that comprises ITVNGTSQNI (SEQ ID NO: 6) into which epitopes of the FG loop or other IgE loops described herein may be substituted or inserted.

Compositions.

Another aspect of the invention is directed to a composition, including, but not limited to, an antigenic, immunogenic, or vaccinogenic composition that comprises a protein construct as disclosed herein comprising a scaffold segment and an IgE motif segment. Typically, such a composition will include a pharmaceutically acceptable excipient or carrier and may further contain an adjuvant or other active agents.

The term carrier encompasses any excipient, binder, diluent, filler, salt, buffer, solubilizer, lipid, stabilizer, or other material well known in the art for use in pharmaceutical formulations, for example, for intravenous administration a carrier may be sodium chloride 0.9% or mixtures of normal saline with glucose or mannose. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia Pa., 2005, which is incorporated herein by reference in its entirety.

An adjuvant is a pharmacological or agent that modifies the effect of other agents. Adjuvants may be added to a protein construct as disclosed herein to boost the humoral or cellular immune responses and produce more anti-IgE antibodies and longer-lasting immunity, thus minimizing the dose of protein construct needed.

Adjuvants that may be compounded with, or otherwise used along with the protein construct disclosed herein include, but are not limited to, inorganic compounds including alum, aluminum hydroxide, aluminum phosphate, calcium phosphate hydroxide; mineral oil or paraffin oil; bacterial products or their immunologically active fractions, such as those derived killed *Bordatella pertussis, Mycobacterium bovis*, or bacterial toxoids; organics such as squalene; detergents such as Quil A, saponins such as *Quillaja*, soybean or *polygala senega*; cytokines such as IL-1, IL-2 or IL-12; Freund's complete adjuvant or Freund's incomplete adjuvant; and food based oils like Adjuvant 65, which is a product based on peanut oil. Those skilled in the medical or immunological arts may select an appropriate adjuvant based on the type of patient and mode of administration of the protein construct of the invention.

For therapeutic purposes, formulations for parenteral administration can be in the form of aqueous or non-aqueous isotonic sterile injection solutions or suspensions. The term parenteral, as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration, preferably in a digestion-resistant form such as an enteric coating. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Administration to the respiratory system may be accomplished using a drug delivery device such as a nebulize to administer the protein construct, DNA encoding it, or antibodies induced to the protein construction in an inhalable form. Nebulizers for treatment of cystic fibrosis, asthma, COPD and other respiratory diseases are known and incorporated by reference to hypertext transfer protocol secure://en.wikipedia.org/wiki/Nebulizer. These include soft mist inhalers, jet nebulizers, ultrasonic wave nebulizers, and nebulizers using vibrating mesh technology.

A metered-dosage inhaler is another drug delivery device that delivers a selected or metered amount of a medication, such as the protein construct disclosed herein, DNA encoding it, or an antibody induced to it. Typically, this device produces and releases an aerosol of micrometer-sized particles that are inhaled. In some cases, the particles may be a dry powder in others as a mist or in a semiliquid form. Metered-dose inhalers and their various components, propellants, excipients and other elements are described by and incorporated by reference to hypertext transfer protocol secure://en.wikipedia.org/wiki/Metered-dose_inhaler. An inhalable composition may be formulated in the form of a hydrofluoroalkane inhaler or HFA (metered dose inhaler or MDI), dry powder inhaler (DPI), or as a nebulizer solution.

Methods of Treatment.

Another aspect of the invention is directed to method for preventing, treating or reducing the severity of a disease, disorder or condition associated with IgE comprising, consisting essentially of, or consisting administering the protein construct as disclosed herein to subject in need thereof; an antibody induced against the protein construct, or DNA encoding the protein construct.

Active Vaccination.

An active vaccine containing an IgE motif containing protein construct disclosed herein may be administered to prevent, treat or reduce the severity of IgE-mediated symptoms. Such symptoms include those commonly associated with allergy or anaphylaxis including, but not limited to "hives" (red blotches or welts that itch), mild to severe swelling on the skin; tearing, redness, or itching of the eyes; a clear discharge, itch, congestion of the nose; an itch, lip swelling, or tongue swelling of the mouth; a tightness, trouble speaking, or trouble inhaling associated with the throat; shortness of breath, rapid breathing, cough, or wheeze associated with the lungs; repeated vomiting, nausea, abdominal pain, or diarrhea associated with the stomach; a weak pulse, loss of consciousness associated with the circulatory system; or anxiety, agitation, loss of consciousness associated with brain or nervous system functions.

The immunogen or vaccine comprising the protein construction may be used to treat IgE-mediated food allergies. Such allergies cause a child's or adult's system to react abnormally when exposed to one or more specific foods such as milk, egg, wheat or nuts. IgE mediated food allergies typically occur quickly within a few minutes to a few hours and are caused by pre-existing allergen-specific immunoglobulin E (IgE) antibody found in a subject's blood stream. The most common food allergens include: milk, egg, soy, wheat, peanut, tree nuts, fish, and shellfish. All of these foods can trigger anaphylaxis, a severe, whole-body allergic reaction) in patients who are allergic. The protein construct as disclosed herein may be used in the treatment or prevention of IgE associated or mediated disorders such as those described above. In some embodiments, the subject will be a male or female no more than 0.5, 1, 2, 3, 4, 5, 6, 7, 8, 9, 10, 12, 15, 18, or 21 years of age. In other embodiments, the subject will be a male or female more than 18, 21, 25, 30, 40, 50, 60, 70, 80 or 90 years of age.

In some embodiments the protein construct is administered parenterally to the subject in need thereof to induce antibodies to IgE. For example, the protein construct or a composition containing it may be administered by subcutaneous, intramuscular, or intravenous routes.

In other embodiments it may be administered to the respiratory system of the subject in need thereof. For example, it may be administered as an aerosol or powder that is sized or formulated to reach and deposit in various areas of the upper respiratory tract such as the nasal cavity, sinuses, pharynx or larynx; or sized and formulated reach and deposit in various areas of the lower respiratory tract such as the trachea, bronchi, diaphragm or lungs.

In other embodiments, the protein construct is administered onto a non-respiratory system mucous membrane, such as those of the eyes, gastrointestinal tract, urinary tract or sexual organs or to the skin of a subject in need thereof.

Passive Vaccination.

In an alternative embodiment, the protein construct is used to induce antibodies against IgE which are passively administered to a subject in need of treatment for an IgE mediated condition. For example, the protein construct is used to produce polyclonal or monoclonal antibodies that recognize IgE. Such antibodies may be of any isotype, such as IgM, IgG, IgA or IgE. Such passive vaccines may be administered parenterally, into the respiratory system, or onto a mucous membrane or skin.

DNA vaccination is a technique for protecting against a disorder or disease by injection with engineered DNA so cells directly produce antigenic IgE determinants or epitopes, producing a protective immunological response or a response the reduces the severity of allergy or other IgE mediated phenomena. DNA vaccines have potential advantages over conventional vaccines, including the ability to induce a wider range of immune response types. In some embodiments of the invention, the protein construct as disclosed herein may be encoded and expressed by a DNA vaccine. The DNA encoding the protein construct is injected into the body and taken up by cells, whose normal metabolic processes synthesize proteins based on the genetic code in the plasmid or other construct that they have taken up. A DNA vaccine may be administered by intramuscular or intradermal delivery, by gene gun, by jet injection or by administration of DNA in liposomal form. In some embodiments, a DNA vaccine, such as a liposome containing DNA encoding the protein construct may be administer to the nasal mucosa or other surfaces of the respiratory system. In some embodiments, DNA encoding the protein construct as disclosed herein may be replicated or synthesized by known methods. The DNA is then formulated for administration to a subject, for example, by pulmonary, intravenous, subcutaneous, intramuscular, intrapulmonary, or intralymphatic administration. DNA-based vaccines and methods of their use are known and are incorporated by reference to Tregoning, J S, et al., *Using Plasmids as DNA Vaccines for Infectious Diseases*. Microbiol Spectr. 2014 Dec.; 2(6). doi: 10.1128/microbiolspec.PLAS-0028-2014; Ramirez, L A, et al., *Therapeutic and prophylactic DNA vaccines for HIV*-1. Expert Opin Biol Ther. 2013 April; 13(4):563-73. doi: 10.1517/14712598.2013.758709; Williams, J A, *Improving DNA vaccine performance through vector design*. Curr Gene Ther. 2014; 14(3):170-89.

Method for Recombinant Production of a Protein Construct.

Another aspect of the invention is directed to a method for making the protein construct disclosed herein. This method typically involves construction of a chimeric DNA molecule that encodes the scaffold and IgE motifs of the protein construct and optionally a protein tag. The chimeric DNA molecule may be constructed by methods known in the art. Once constructed it is transformed or transfected into a host cell usually in the form of an expression vector which then expresses the protein construct.

Recombinant or chimeric DNA encoding a protein construct as disclosed herein, including both scaffold segments and IgE motif segments, can be designed by careful selection and evaluation of putative scaffold and IgE motif sequences as shown by the Example. Typically, this will involve screening a protein data base for a suitable scaffold protein, evaluating the conformation of particular scaffolds and IgE motifs by modelling then on a computer, for example, the conformation of combinations of an IgE motif comprising an FG loop of SEQ ID NO: 2 or a R loop of SEQ ID NO: 3, and scaffolds such as that of 1YN3 chain, and engineering the sequence of the protein construct so that it folds in a way to efficiently present the IgE FG loop or R loop to the immune system.

A search on the entire PDB database for possible scaffolds for the IgE motif was performed using Rosetta which can also be performed using the MotifGraftMover from PyRosetta. Once several scaffolds were found each scaffold was sequence designed using the RosettaDesign fixed-backbone protocol to find a sequence that will fold to the desired backbone, this procedure was followed by forward folding using the AbinitioRelax protocol in Rosetta to simulate the folding of the newly designed structure. Several rounds of design and forward folding were performed on each structure (sometimes using manual residue mutations) until a successful forward fold was achieved. Since the backbone of the Y1N3 structure was ideal all the sequence designs were successful at the forward fold simulations. A flowchart showing the preferred steps of this process is shown in FIG. 8.

Additionally, the 1YN3, 3LDZ, and 3EGR scaffolds were sequence designed and their sequences were changed from the original published sequences. The computational algorithm used was standard and simple. In addition to a high level (e.g, at least 95%) of sequence identity, the backbone similarity can be described through a "root means square deviation" metric value. Advantageously a cutoff point of a RMSD<1, 2, 3, 4, 5, 6, 7, 8, 9 to 10 angstroms can be used because the closer the RMSD value is to 0 the more identical the backbone is to a designed scaffold; see e.g. Kufareva, Irina, and Ruben Abagyan. *Methods of protein structure comparison.* Methods in molecular biology (Clifton, N.J.) vol. 857 (2012): 231-57. doi:10.1007/978-1-61779-588-6_10 which is incorporated by reference.

The root-mean-square deviation of atomic positions or simply root-mean-square deviation, RMSD, is a measure of the average distance between the atoms, usually backbone atoms, of superimposed proteins. Root mean square deviation (RMSD) between two structures can be determined as is well-known to one of skill in the art, for example, using MOE v2016.0802 (Chemical Computing Group). Similarity is typically measured in three-dimensional structure by the RMSD of the Cα atomic coordinates after optimal rigid body superposition. For a variant scaffold protein or variant IgE motif as disclosed herein the atomic positions of backbone atoms may vary by up to 1, 2, 3, 4, 5, 6, 7, 8, 9 or 10 angstroms from a reference protein such as a protein described by SEQ ID NOS: 5, 17, 19 or 21 or to a segment of reference protein having at least 10, 15, 20, 25 or 30 contiguous residues. Preferably, the RMSD is calculated from the full length of the reference protein structure and not from a shorter segment.

Recombinant Expression.

The protein constructs as disclosed herein may be made by any technique known to those of skill in the art, including by expression of the constructs through standard molecular biological techniques including by recombinant protein expression or by chemical synthesis. Typically, for recombinant expression of a protein construct, DNA encoding the construct is synthesized or spliced together from a source of the scaffold and motif DNA segments, and is cloned downstream of a promoter in an expression vector. This vector is then introduced into a host cell, and the cell's protein synthesis machinery produces the protein construct. Thus, another embodiment of the invention is a method for expressing DNA encoding a protein construct as disclosed herein, thereby producing the protein construct.

The term "protein construct" as used herein refers to a protein comprising a scaffold segment as described herein and an IgE motif segment, preferably where the IgE motif segment is substituted for a stretch of amino acids in the scaffold protein segment.

A "recombinant host cell," as used herein, is a cell comprising one or more recombinant nucleic acid sequences or transgenes not naturally present in the cell which encode the protein construct of the invention. These transgenes are expressed in the host cell to produce recombinant protein constructs comprising the IgE motif described herein that are encoded by these nucleic acid sequences when these cells are cultured under conditions conducive to expression of nucleic acid sequences. In some instances, the host cell may be cell within a subject which received a DNA-based vaccine. The host cell, as used herein, can be present in the form of a culture from a clone that is derived from a single host cell wherein the recombinant DNA or transgenes have been introduced. It is well known to those skilled in the art that sequences capable of driving such expression can be functionally linked to the nucleic acid sequences encoding the recombinant proteins, such as the protein construct disclosed herein.

"Functionally linked" is meant to describe that the nucleic acid sequences encoding the protein construct or fragments or precursors thereof which are linked to the sequences capable of driving expression such that these sequences can drive expression of the protein construct or precursors thereof.

Useful expression systems are available in the art, for example, the mammalian protein expression, insect protein expression, yeast protein expression, bacterial protein expression, or algal protein expression systems of Invitrogen. Where the sequence encoding the polypeptide of interest, namely the protein construct of the invention, is properly inserted with reference to sequences governing the transcription and translation of the encoded polypeptide, the resulting expression cassette is useful to produce the polypeptide of interest, referred to as expression. Sequences driving expression may include promoters, enhancers and the like, and combinations thereof. These should be capable of functioning in the host cell, thereby driving expression of the nucleic acid sequences that are functionally linked to them. Promoters can be constitutive or regulated and can be obtained from various sources, including viruses, prokaryotic or eukaryotic sources, or artificially designed. Expression of nucleic acids of interest may be from the natural promoter or derivative thereof or from an entirely heterologous promoter. Any promoter or enhancer/promoter capable of driving expression of the sequence of interest in the host cell is suitable in the invention. The skilled artisan will be aware that the expression sequences used in the invention may suitably be combined with elements that can stabilize or enhance expression. These may enhance the stability and/or levels of expression.

Protein production in recombinant host cells has been extensively described, e.g., in Current Protocols in Protein Science, *Production of Recombinant Proteins*, Jan. 1, 2018 (updated Oct. 7, 2019), Online ISSN:1934-3663, the entirety of which is incorporated herein by reference. Culturing a cell is done to enable it to metabolize, grow, divide, and/or produce recombinant proteins of interest. This can be accomplished by methods well known to persons skilled in the art and includes, but is not limited to, providing nutrients for the cell. Such methods comprise growth adhering to surfaces, growth in suspension, or combinations thereof. Several culturing conditions can be optimized by methods well known in the art to optimize protein production yields. Culturing can be done, for instance, in dishes, roller bottles or in bioreactors, using batch, fed-batch, continuous systems, hollow fiber, and the like.

"Host cells," may be any host cell capable of expressing recombinant DNA molecules encoding the protein construct presenting IgE epitopes, including bacteria such as *Escherichia* (e.g., *E. coli*), *Enterobacter, Salmonella, Bacillus, Pseudomonas, Streptomyces*, yeasts such as *S. cerevisiae, K lactis, P. pastoris, Candida*, or *yarrowia*, filamentous fungi such as *Neurospora, Aspergillus oryzae, Aspergillus nidulans* and *Aspergillus niger*, insect cells such as *Spodoptera frugiperda* SF-9 or SF-21 cells, mammalian cells such as Chinese hamster ovary (CHO) cells, BHK cells, mouse cells including SP2/0 cells and NS-0 myeloma cells, primate cells such as COS and Vero cells, MDCK cells, BRL 3A cells, and the like.

The protein constructs are expressed in the host cells and may be recovered from the cells or, preferably, from the cell culture medium, by methods generally known to persons skilled in the art. Such methods may include precipitation, centrifugation, filtration, size-exclusion chromatography, affinity chromatography, cation- and/or anion-exchange chromatography, hydrophobic interaction chromatography, and the like.

Codon optimization. A protein construct as disclosed herein may be encoded by a polynucleotide or vector comprising a polynucleotide that has been codon optimized for expression in a particular host cell. Thus, different functionally equivalent codons that encode the same amino acid may be substituted for one another, such as the six codons for arginine, leucine, or serine, the four codons for alanine, glycine, proline, threonine, or valine etc. Codon optimization methods or programs which optimize codon usage for various host cells including those disclosed herein, are incorporated by reference to hypertext transfer protocol secure://www.novoprolabs.com/tools/codon-optimization; hypertext transfer protocol secure://academic.oup.com/bioinformatics/article/30/15/2210/2391162; and hypertext transfer protocol://bioinfo.bti.a-star.edu.sg/COOL/. In some embodiments, a polynucleotide sequence encoding a protein construct as disclosed herein may be optimized using one of the above mentioned methods or programs or a publically or commercially available program for expression by human or mammalian cells, such as by Chinese hamster ovary cells, myeloma lymphoblastoid cells such as NS0 cells, or by fully human host cells such as human embryonic kidney cells like HEK-293, human embryonic retinal cells like Crucell's Per.C6, human amniocyte cells like Glycotope and CEVEC; by baculovirus-infected cells such as Sf9, Sf21, High Five strains; filamentous fungi such as by yeasts such as *S. cerevisiae* or *Pichia pastoris*, or by prokaryotic expression systems such as those using *Escherichia coli, corynebacterium, Bacillus subtilis*, or *Pseudomonas fluorescens*.

Purification of the protein construct. The recombinantly expressed protein construct can be purified by methods known in the art including by solvent or surfactant extraction, removal of insoluble components by filtration or centrifugation and affinity purification. In some embodiments, the protein construct is purified by affinity purification using antibodies that bind to the scaffold, IgE motif or to an expression or purification tag attached to the protein construct.

Protein tags may be produced by grafting DNA encoding them onto a polynucleotide construct encoding the protein construct and then expressing the grafted protein construct. Often these tags are removable by chemical agents or by enzymatic means, such as proteolysis or intein splicing. Tags are attached to proteins for various purposes including to facilitate their purification by antibodies or other ligands that bind to the tag. Such tags include but are not limited to affinity tags which are appended to a protein so that it can be purified from a crude biological source using an affinity technique. These include chitin binding protein (CBP), maltose binding protein (MBP), Strep-tag and glutathione-S-transferase (GST). The poly(His) tag is a widely used protein tag, which binds to metal matrices. Other protein tags include those described by and incorporated by reference to hypertext transfer protocol secure://en.wikipedia.org/wiki/Protein tag (as last accessed Jan. 8, 2020). Those skill in the art may select an appropriate tag and/or other mode of purification to isolate the protein construct as disclosed herein. The proteins may be expressed in systems, such as those using prokaryotic vectors and cells, that do not glycosylate proteins or in systems using eukaryotic vectors and cells, such as Chinese Hamster Ovary cells, which glycosylate protein. Preferably in terms of function, these proteins are soluble in a culture medium, in the cytoplasm of host cells, and in physiological acceptable solvents. The degree of solubility depends also on selection of the expression vector and host cells as well as choice of solvent and other chemical and physical factors such as pH, salt content, and temperature.

Examples

The following steps were used to generate a database of scaffold structures as well as isolate the IgE motif, graft it onto a scaffold, then design the scaffold to fold onto the designed structure.

Motif Determination and Excision.

The FG motif is part of the Ig epsilon C region, chain B (2Y7Q_B; SEQ ID NO: 1). This motif comprises residues 420-429 of this sequence (residues 200-209 of SEQ ID NO: 1): VTHPHLPRAL (SEQ ID NO: 2) and chosen due to its very close proximity to the receptor binding site ("R") which comprises residues 331-338 of 2Y7Q chain B: SNPRGVSA, residues 111-118 of SEQ ID NO: 3). The numbering is PBD centric and takes into account that chain B of the 1YN3 structure starts at position 229 of the PBD structure (and not the FASTA sequence from NLM).

The FG motif is a ridged structure and the motif resembles a heart shape with an anchoring 425 lysine pointing into the core fixing its shape. The FG motif was selected for further work because the receptor binding site ("R") was not anchored and had a higher degree of movement its surrounding area and the was not as well modelled in the crystal structure.

The FG motif was isolated along with the IgE receptor, 2Y7Q chain A; SEQ ID NO: 4, as separate files in preparation for grafting.

Scaffold Database Generation.

The scaffold database was generated by downloading the entire PDB database, then isolating only protein structures and separating each chain into separate .pdb files. Each structure was cleaned (removed of any non-peptide atoms) then passed through (scored) by the Rosetta modelling software to make sure each structure will not crash the software. Structures that were not satisfactory were discarded. Such procedures are described by and incorporated by reference to Leaver-Fay, et al. 2011. *ROSETTA3: an object-oriented software suite for the simulation and design of macromolecules*. Methods Enzymol 487: 545-74. doi: 10.1016/b978-0-12-381270-4.00019-6. For an alternative embodiment a script was developed that produces a better, smaller, and more targeted database, but was not used here.

Motif Grafting.

The desired motif between positions 420 and 429 in the 2Y7Q chain B protein was isolated along with the receptor in chain A then a grafting search was performed that matched the backbone of the motif to backbones within the database, if there was a match within an RMSD value of 1.0 A or less the motif was grafted onto the scaffold structure (replacing the original backbone) and measured for its clash with the receptor (to make sure the backbone was not grafted inward or was buried within the structure). This protocol was developed by and is incorporated by reference to Azoitei, M. L., et al., 2011. *Computation-guided backbone grafting of a discontinuous motif onto a protein scaffold*. Science 334: 373-376. doi: 10.1126/science.1209368; and Azoitei, M. L., et al., 2012. *Computational design of high-affinity epitope scaffolds by backbone grafting of a linear epitope*. J Mol Biol 415: 175-92. doi: 10.1016/j.jmb.2011.10.003.

Selective Fixed-Backbone Design.

The final structure was tested for folding and failed. Accordingly, some human guided mutations were employed to push the structure to fold onto its designed structure. After many failed attempts the fixed-backbone design protocol was employed, where the side chain sequence of the structure was stochastically mutated and packed using a rotated library to find the lowest energy structure that would fold into the designed structure. Such procedures are described by and incorporated by reference to Kuhlman, B., et al., 2003. *Design of a novel globular protein fold with atomic-level accuracy*. Science 302: 1364-1368. doi: 10.1126/science.1089427; Dantas, G., et al., 2003. *A large scale test of computational protein design: folding and stability of nine completely redesigned globular proteins*. J Mol Biol 332: 449-60; Leaver-Fay, A., et al., 2005. *An adaptive dynamic programming algorithm for the side chain placement problem*. Pac Symp Biocomput 16-27; Hu, X., et al., 2007. *High-resolution design of a protein loop*. Proc Natl Acad Sci USA 104: 17668-73. doi: 10.1073/pnas.0707977104; and Andrew Leaver-Fay, et al. 2005. *Rotamer-pair energy calculations using a trie data structure*. Mallorca, Spain: Springer-Verlag.

Using this protocol, the inventors changed the Rosetta Energy Function 2015 (REF15). energy function weights to include aa_rep 1.0, aspartimid_penalty 1.0, buried_unsatisfied_penalty 1.0, and approximate_buried_unsat_penalt 5.0 which assisted in designing an adequate sequence that both fits the backbone structure and increases the energy gap between the desired structure and any other possible undesired fold.

Folding Simulation.

To get inside into whether the design process was successful, the structures were simulated for their folding using the Abinitio protocol, where the sequence is folded using first principals and some statistical weights through the REF15 scoring function, and to reduce the folding space and speed up the search for the global minima fragment were developed from the FASTA sequence, were backbone torsion angles are statistically analysed and inserted to help the algorithm fold the structure. Such procedures are described by an incorporated by reference to Raman, S., et al., 2009. *Structure prediction for GASPS with all atom refinement using Rosetta*. Proteins 77 Suppl 9: 89-99. doi: 10.1002/prot.22540; Bradley, P., et al., 2005. *Toward high-resolution de novo structure prediction for small proteins*. Science 309: 1868-71. doi: 10.1126/science.1113801; Bonneau, R., et al. 2002. *De novo prediction of three-dimensional structures for major protein families*. J Mol Biol 322: 65-78; Bonneau, R., et al., 2001. *Rosetta in CASP4: progress in ab initio protein structure prediction*. Proteins Suppl 5: 119-26; Simons, K. T., et al. 1999. *Improved recognition of native-like protein structures using a combination of sequence-dependent and sequence-independent features of proteins*. Proteins 34: 82-95; and Simons, K. T., et al., 1997. *Assembly of protein tertiary structures from fragments with similar local sequences using simulated annealing and Bayesian scoring functions*. J Mal Biol 268: 209-25. doi: 10.1006/jmbi.1997.0959.

Results.

Figure 1:
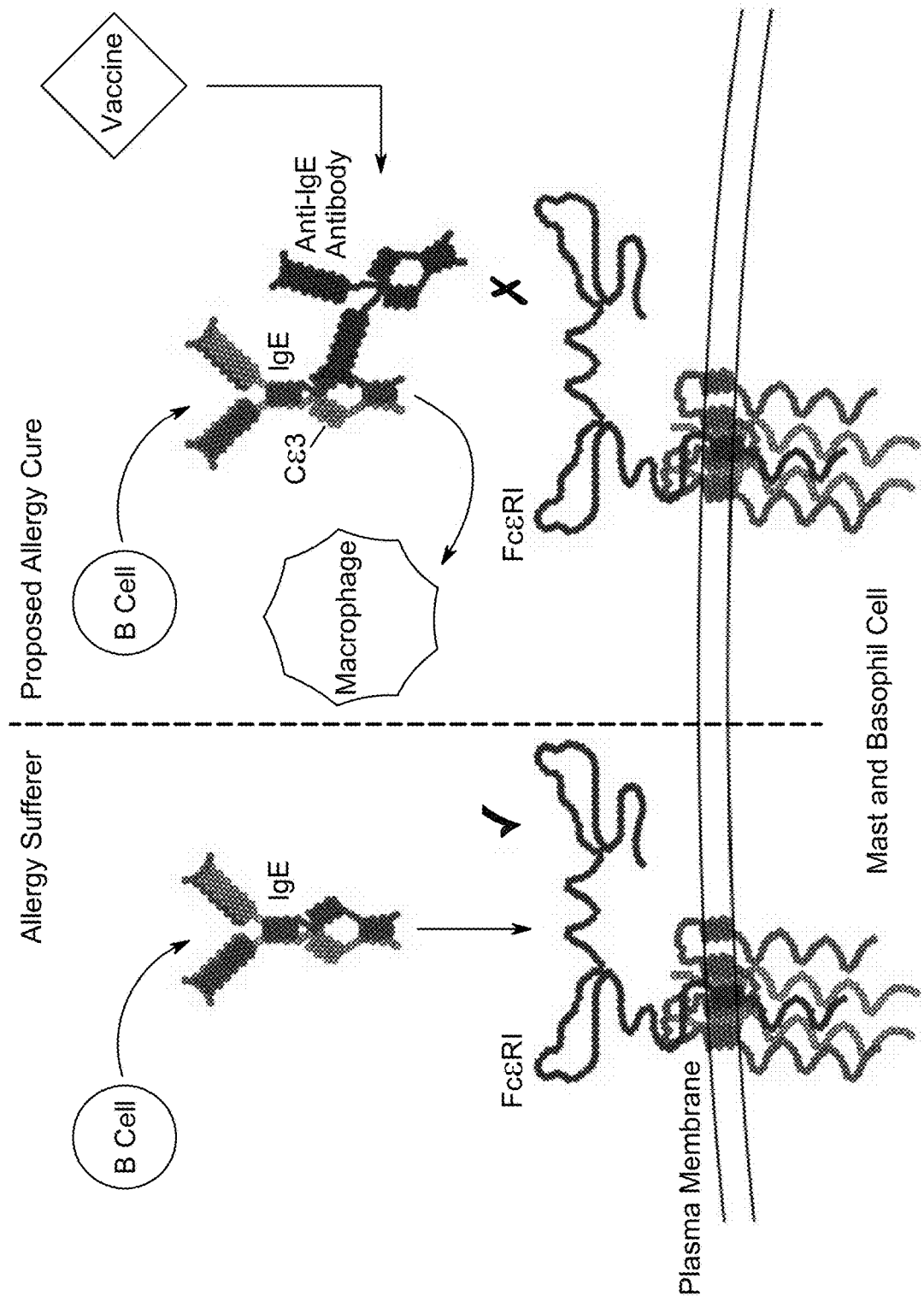
FIG. 1 summarizes the pan-anti-allergy vaccine therapy concept which involves administering a vaccine that produces antibodies against allergy inducing IgE molecules expressed by the immunized patient. The anti-IgE antibodies induced by the vaccine neutralize allergy-inducing IgE, thus disrupting the entire allergy pathway and reducing the severity of allergic symptoms or disease.
Figure 2:
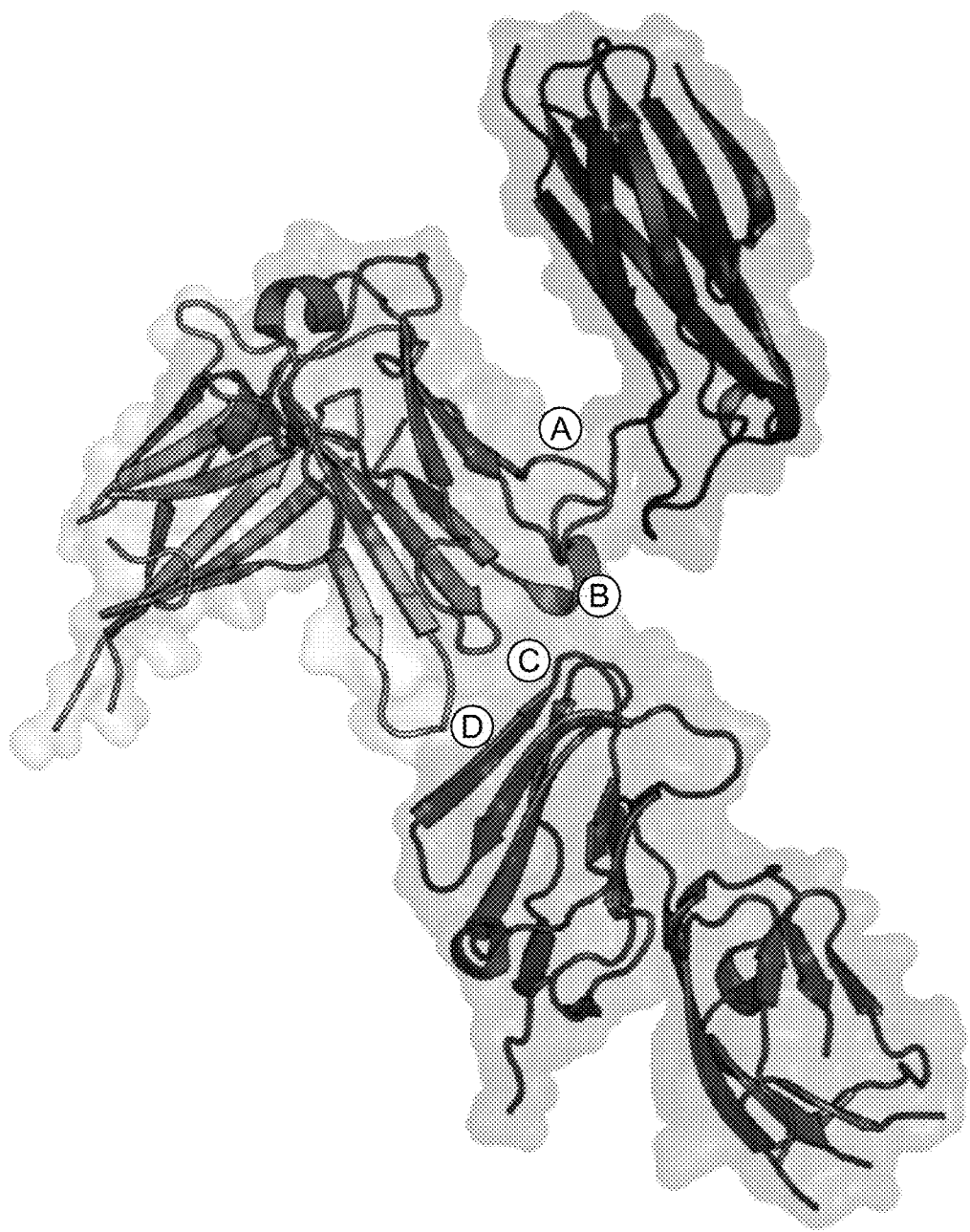
FIG. 2 illustrates the structure of the human IgE as bound to its FcεR1α receptor (Protein Databank: 2Y7Q). The capital letters denote the different loops that are closest in proximity to, or which form hydrogen bonds with, the receptor when bound. The coding is as follows: (A) for the FG loop, (B) for the R loop, (C) for the BC loop, and (D) for the DE loop.
Figure 3B:
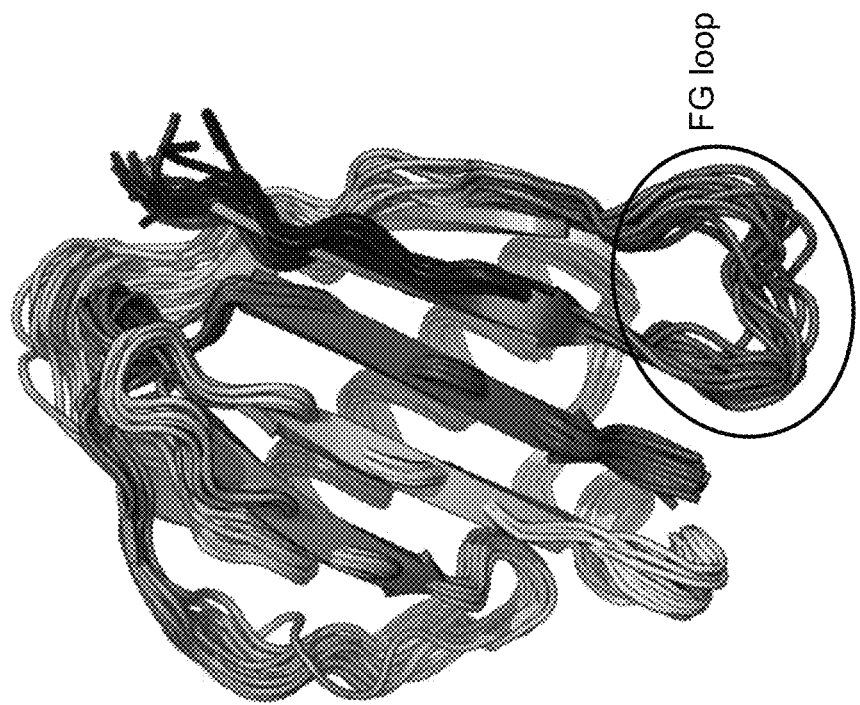
FIG. 3B shows one of the structures (1YN3) that successfully grafted the FG loop motif showing better motif stability (average RMSD=0.62 Å to the natives motif).
Figure 3A:
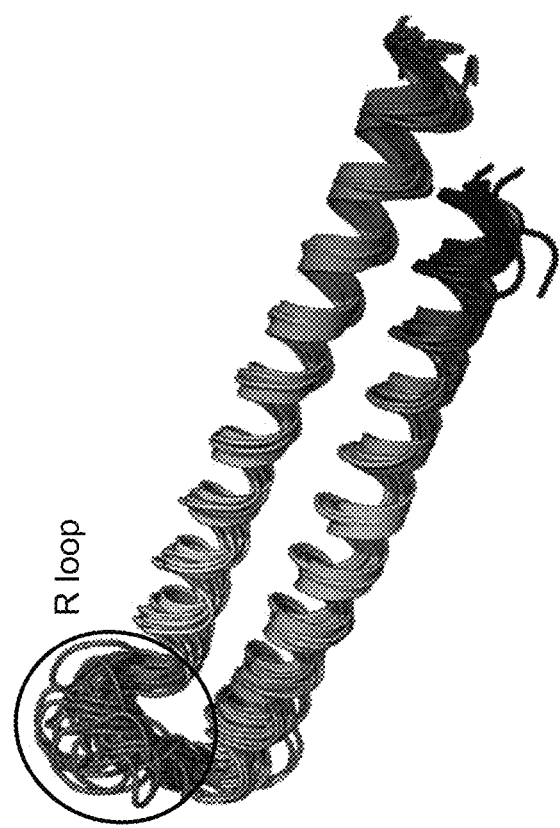
FIG. 3A shows one of the structures (PDB: 3Q4H; SEQ ID NO: 20) that successfully grafted the R loop motif ("R loop"), showing the large variability of the motif backbone since it lacked an anchor (average RMSD=1.29 Å to the natives motif). All chains have the same structure, but chain B is preferred. The SNPRGVSA (SEQ ID NO: 3) from human IgE represents the R loop which was grafted on to 3Q4H to replace the QGDTGMTY (SEQ ID NO: 23) sequence. M here is selenomethionine (MSE) between residues 44-51 of the PDB file from the RCSB server.
Figure 4C:
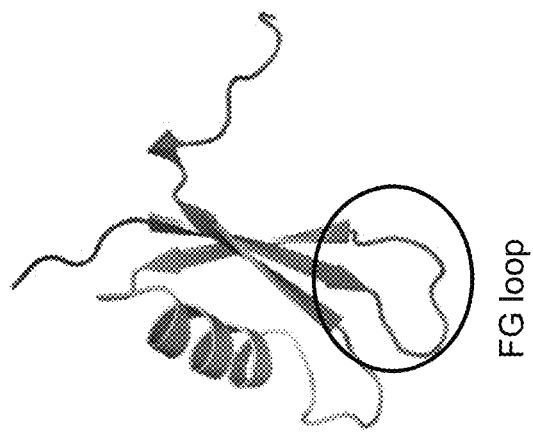
Figure 4B:
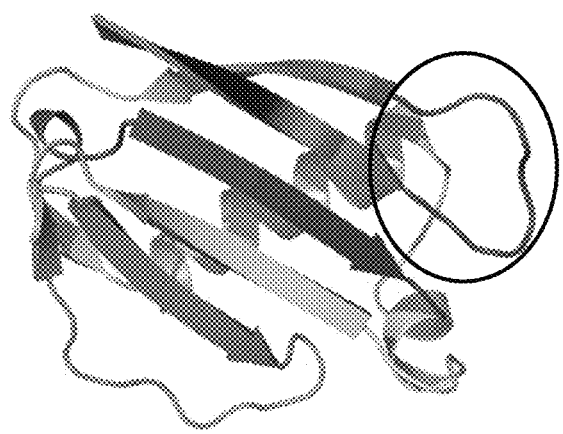
Figure 4A:
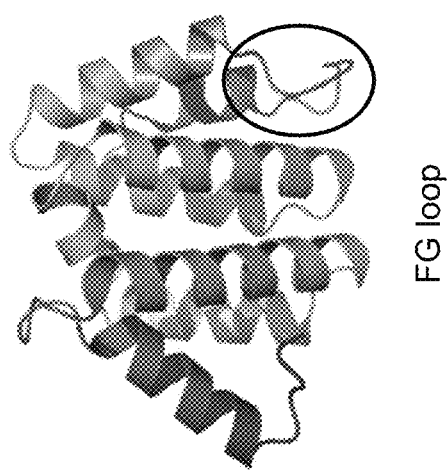
Figure 5:
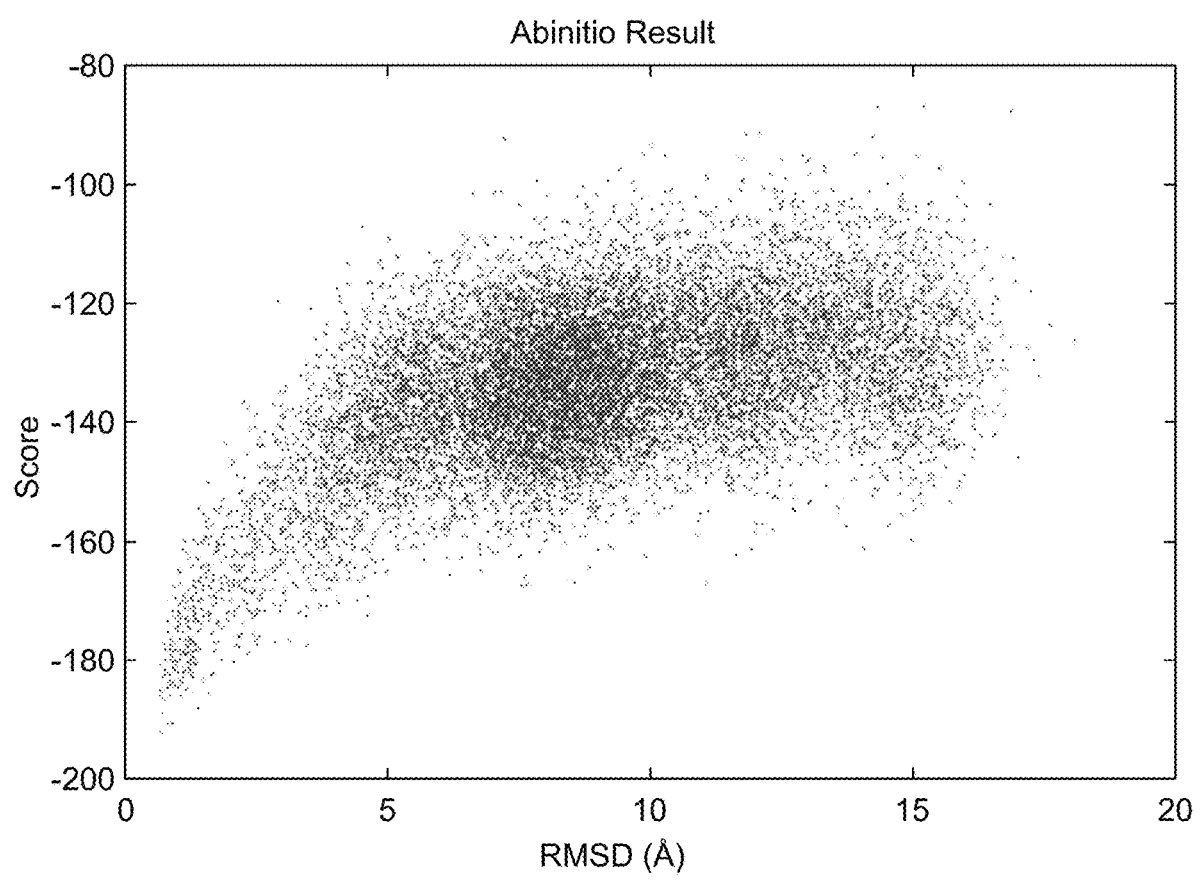
Figure 6C:
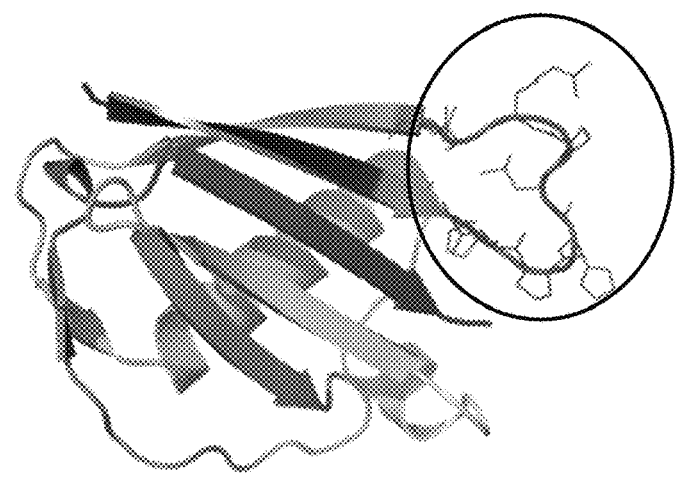
Figure 6B:
Figure 6A:
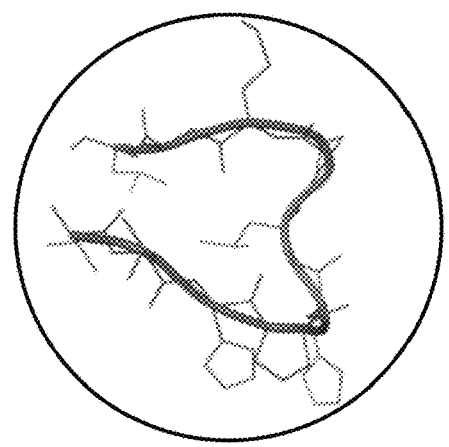

Analysis of the motif position revealed that the R loop and the FG loop from the human IgE (1Y7Q) were the best candidates for an IgE-targeted vaccine due to their proximity to the binding site on the a chain of the FcεRI receptor (FIG. 2).

After several attempts at grafting and designing the R loop, the FG loop was selected for further work because it has an inward pointing leucine resulting in a ridged loop structure. In contrast, the R loop was found to have a high degree of angle freedom which resulted in a wide range of different structures when grafted, see FIG. 3.

The scaffold search algorithm resulted in the FG loop motif being grafted onto the 1YN3 structure as well as several other structures; see FIG. 4. The structure and other description of 1YN3 and EAPs in general is incorporated by reference to Geisbrecht, B. V., et al. 2005. *The crystal structures of extracellular adherence protein ("EAP") domains from Staphylococcus aureus reveal an unexpected homology to bacterial superantigens*. J Biol Chem 280: 17243-50. doi: 10.1074/jbc.M412311200.

The 1YN3 structure (SEQ ID NO: 5) was chosen since it had a backbone that was easily simulated by forward folding using the AbinitioRelax protocol; see FIG. 5 and because it would be easy to crystallize for structural evaluation. The 1YN3 protein is an EAP domain from *Staphylococcus aureus* which has been previously expressed in *Escherichia coli* host cells prior to its crystallization.

The FG motif was grafted between positions 164 and 173 in the 1YN3 structure and replaced the sequence ITVNGTSQNI (SEQ ID NO: 6) with VTHPHLPRAL (SEQ ID NO: 2); see FIG. 6. However, the inventors determined using AbinitioRelax that the freshly grafted structure failed a forward fold, and attributed this failure to the addition of the motif backbone and side chains which severely disrupted the stability of the entire structure.

To overcome this problem, with the exception of the FG motif, the entire secondary structure was redesigned by changing the side chains while fixing the backbone to stabilize the structure and accommodate the redesigned motif backbone and side chains.

To compensate for a failure rate between a successful forward fold and a successful crystal structure, the inventors repeated the sequence design step ten times producing ten structures (SEQ ID NOS: 7-16) all of which passed a successful forward fold; FIGS. 7A-7AD. This process increases the probability of synthesizing a correctly folded vaccine structure as determined by a crystallography evaluation. The ten structures of SEQ ID NOS: 7-16 each contain the IgE motif sequence, but flanking sequences have been designed using a Rosetta Design fixed-backbone computational protocol. This protocol uses a Monte Carlo based method to design protein sequences that fit the backbone of 1YN3. The RosettaDesign protocol also uses the REF2015 energy function to determine the best sequence for each run.

All structures were predicted to fold within a sub angstrom level of the designed structure, giving high confidence that a biologically synthesized protein construct would retain the same structure. Preferably, prior to structural evaluation in vivo, each structure is crystallized to definitively confirm the resulting protein construct is correctly folded.

As shown herein, the inventors have developed a protocol for computationally designing proteins that correctly display the three dimensional structure of a strategic motif of the IgE molecule, where the motif is grafted onto scaffold proteins, opening the possibility of using such protein structures as a vaccine against self-IgE and permanently shutting down the allergy pathway regardless of the offending allergen (a pan-anti-allergy vaccine).

The resulting structures showed agreement in their final folds when simulated with different computational folding algorithms and can be verified by solving their structures through X-Ray crystallography.

Furthermore, the efficacy of the proteins in pushing the immune system into developing high-affinity antibodies against self-IgE at a higher binding affinity than IgE/FceRI receptor's binding affinity could not be computationally simulated, and thus must be tested on animals to reach a definitive answer. The script that was used to design these proteins is available at this GitHub repository (hypertext transfer protocol secure://github.com/sarisabban/VaxDesign; last accessed Apr. 22, 2020) which includes an extensive README file that explains how to use it.

Terminology.

Terminology used herein is for the purpose of describing particular embodiments only and is not intended to be limiting of the invention.

As used herein, the singular forms "a", "an" and "the" are intended to include the plural forms as well, unless the context clearly indicates otherwise.

The terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any or all combinations of one or more of the associated items listed and may be abbreviated as "/".

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

Polynucleotide sequences encoding the protein sequences disclosed herein are described by reference to the corresponding protein sequence. Such polynucleotide sequences are deduced using the genetic code and encompass any codons which encode the corresponding protein. Due to the degeneracy of the genetic code multiple polynucleotide codons may be used to encode the same amino acid residue. In some embodiments, polynucleotide sequences may be codon optimized for expression in a particular host cell. However, the polynucleotide sequences described herein also encompass those native polynucleotide sequences already known in the art, such as those associated with the various accession numbers of the proteins disclosed herein.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears. Specifically, unless otherwise specified the accession numbers such as those from the PDB refer to the last versions available on the filing date of this application. All such accession numbers, and the ancillary information they contain, are incorporated by reference.

The invention claimed is:

1. A protein construct, comprising:
a scaffold segment and a motif segment,
wherein the scaffold segment comprises a protein that is exogenous to immunoglobulin E ("IgE") which has been modified by insertion of the motif segment into the scaffold segment,
wherein the scaffold segment comprises an extracellular adherence protein (EAP) IYN3 chain A (SEQ ID NO: 5), and
wherein the motif segment comprises an IgE FG loop (SEQ ID NO: 2) and
wherein the construct comprises any one of SEQ ID NOS: 7-16.

2. A composition comprising the protein construct of claim 1 and a pharmaceutically acceptable excipient or carrier.

3. The composition of claim 2, further comprising at least one adjuvant.

4. A method for making the protein construct of claim 1, comprising:
computer modelling of scaffold proteins of the extracellular adherence protein (EAP) domain of *Staphylococcus aureus* that is EAP IYN3 chain A of SEQ ID NO:

5 when modified by insertion of an IgE motif comprising an FG loop (SEQ ID NO: 2), redesigning the portion of the scaffold containing the FG loop so that it folds in a way to present the FG loop to the immune system thereby describing structure of the protein construct;

synthesizing DNA encoding the protein construct, and expressing the DNA in a suitable host cell, thereby producing the protein construct;

wherein the construct is any one of those of SEQ ID NOS: 7-16.

5. The protein construct of claim 1 comprising SEQ ID NO: 7.

6. The protein construct of claim 1 comprising SEQ ID NO: 8.

7. The protein construct of claim 1 comprising SEQ ID NO: 9.

8. The protein construct of claim 1 comprising SEQ ID NO: 10.

9. The protein construct of claim 1 comprising SEQ ID NO:11.

10. The protein construct of claim 1 comprising SEQ ID NO: 12.

11. The protein construct of claim 1 comprising SEQ ID NO: 13.

12. The protein construct of claim 1 comprising SEQ ID NO: 14.

13. The protein construct of claim 1 comprising SEQ ID NO: 15.

14. The protein construct of claim 1 comprising SEQ ID NO: 16.

* * * * *